United States Patent
Miller et al.

(10) Patent No.: US 10,535,133 B2
(45) Date of Patent: Jan. 14, 2020

(54) AUTOMATED ANATOMICAL LABELING BY MULTI-CONTRAST DIFFEOMORPHIC PROBABILITY FUSION

(71) Applicant: The Johns Hopkins University, Baltimore, MD (US)

(72) Inventors: Michael I. Miller, Pikesville, MD (US); Susumu Mori, Ellicott City, MD (US); Xiaoying Tang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 694 days.

(21) Appl. No.: 15/112,164

(22) PCT Filed: Jan. 20, 2015

(86) PCT No.: PCT/US2015/012092
§ 371 (c)(1),
(2) Date: Jul. 15, 2016

(87) PCT Pub. No.: WO2015/109331
PCT Pub. Date: Jul. 23, 2015

(65) Prior Publication Data
US 2016/0343127 A1    Nov. 24, 2016

Related U.S. Application Data

(60) Provisional application No. 61/928,772, filed on Jan. 17, 2014.

(51) Int. Cl.
*G06T 7/00*    (2017.01)
*G06T 7/174*    (2017.01)
(Continued)

(52) U.S. Cl.
CPC ............ *G06T 7/0012* (2013.01); *A61B 5/055* (2013.01); *A61B 6/032* (2013.01); *A61B 6/037* (2013.01);
(Continued)

(58) Field of Classification Search
None
See application file for complete search history.

(56) References Cited

U.S. PATENT DOCUMENTS

| | | | | |
|---|---|---|---|---|
| 8,170,330 B2 * | 5/2012 | Kiraly | ............... | G06K 9/6269 382/156 |
| 2011/0235884 A1 * | 9/2011 | Schreibmann | ......... | A61B 6/037 382/131 |

(Continued)

OTHER PUBLICATIONS

Bajcsy et al., "A Computerized System for the Elastic Matching of Deformed Radiographic Images to Idealized Atlas Images," Journal of Computer Assisted Tomography, 7(4): 618-625 (1983).
(Continued)

*Primary Examiner* — Matthew C Bella
*Assistant Examiner* — Brian D Shin
(74) *Attorney, Agent, or Firm* — Venable LLP; Henry J. Daley

(57) ABSTRACT

A computer-implemented method, system and non-transitory computer readable storage medium for classifying a region of interest of a subject, including receiving imaging data comprising at least one image element, the imaging data comprising the region of interest of the subject; providing a plurality of atlases, each of the plurality of atlases having a candidate region that corresponds to the region of interest of the imaging data, each of the plurality of atlases having at least one image element with associated location and property information; co-registering the plurality of atlases to the imaging data, using at least one processor; assigning a probability to generate a labeling parameter for the region of
(Continued)

S110 – Receiving Imaging Data

S120 – Providing a Plurality of Atlases

S130 – Co-Registering the Plurality of Atlases to the Imaging Data

S140 – Assigning a Probability to Generate a Labeling Parameter

S150 – Classifying the Region of Interest

S160 – Suggesting an Anatomical Feature interest, the probability being associated with each atlas; and classifying the region of interest of the subject based on the assigning.

27 Claims, 10 Drawing Sheets

(51) Int. Cl.
```
A61B 6/03      (2006.01)
G06K 9/46      (2006.01)
A61B 5/055     (2006.01)
G06T 7/143     (2017.01)
G06T 7/11      (2017.01)
G06T 7/33      (2017.01)
A61B 6/00      (2006.01)
A61B 8/08      (2006.01)
G06K 9/52      (2006.01)
G06K 9/62      (2006.01)
```
(52) U.S. Cl.
CPC .......... *A61B 6/5211* (2013.01); *A61B 8/5215* (2013.01); *G06K 9/4671* (2013.01); *G06K 9/52* (2013.01); *G06K 9/6267* (2013.01); *G06T 7/11* (2017.01); *G06T 7/143* (2017.01); *G06T 7/174* (2017.01); *G06T 7/33* (2017.01); *G06K 2009/4666* (2013.01); *G06T 2207/10081* (2013.01); *G06T 2207/10088* (2013.01); *G06T 2207/10104* (2013.01); *G06T 2207/20021* (2013.01); *G06T 2207/20076* (2013.01); *G06T 2207/20128* (2013.01); *G06T 2207/30016* (2013.01)

(56) References Cited

U.S. PATENT DOCUMENTS

| 2012/0177263 A1 | 7/2012 | Akinyemi et al. |
| 2012/0281900 A1 | 11/2012 | Rueckert et al. |
| 2012/0320055 A1* | 12/2012 | Pekar ............... G06T 7/0012 345/424 |
| 2015/0086096 A1* | 3/2015 | Liu ............... G06T 7/149 382/131 |

OTHER PUBLICATIONS

Aljabar et al., "Multi-atlas based segmentation of brain images: Atlas selection and its effect on accuracy," Neuroimage 46: 726-738 (2009).
Allassonniere et al., "Towards a coherent statistical framework for dense deformable template estimation," Journal of the Royal Statistical Society: Series B (Statistical Methodology) 69: 3-29 (2007).
Artaechevarria et al., "Combination strategies in multi-atlas image segmentation: Application to brain MR data. Medical Imaging," IEEE Transactions on 28: 1266-1277 (2009).
Asman et al., "Formulating spatially varying performance in the statistical fusion framework," Medical Imaging, IEEE Transactions on 31: 1326-1336 (2012).
Awate et al., "A fuzzy, nonparametric segmentation framework for DTI and MRI analysis," Inf Process Med Imaging 20: 296-307 (2007).
Baillard et al., "Robust 3D segmentation of anatomical structures with Level Sets," 1935: 236-245 (2000).
Baillard et al., "Segmentation of brain 3D MR images using level sets and dense registration," Med Image Anal 5: 185-194 (2001).
Bajcsy et al., "Multiresolution elastic matching," Computer Vision, Graphics, and Image Processing 46: 1-21 (1989).
Beg et al., "Computing large deformation metric mappings via geodesic flows of diffeomorphisms," International Journal of Computer Vision 61: 139-157 (2005).

Carmichael et al., "Atlas-based hippocampus segmentation in alzheimer's disease and mild cognitive impairment," Neuroimage 27: 979-990 (2005).
Catani et al., "A diffusion tensor imaging tractography atlas for virtual in vivo dissections," Cortex 44: 1105-1132 (2008).
Ceritoglu et al., "Multi-contrast large deformation diffeomorphic metric mapping for diffusion tensor imaging," Neuroimage 47: 618-627 (2009).
Christensen et al., "Volumetric transformation of brain anatomy," IEEE Trans Med Imaging 16: 864-877 (1997).
Collins et al., "Animal: Validation and applications of nonlinear registration-based segmentation," Intern. J. Pattern Recognit. Artif. Intel. 11: 1271-1294 (1997).
Collins et al., "Automatic 3-D model-based neuroanatomical segmentation," Hum Brain Mapp 3: 190-208 (1995).
Cootes et al., "Use of active shape models for locating structures in medical images," Image and Vision Computing 12: 355-365 (1994).
Coupe et al., "Patch-based segmentation using expert priors: Application to hippocampus and ventricle segmentation," Neuroimage 54: 940-954 (2011).
Crum et al., "Automated hippocampal segmentation by regional fluid registration of serial MRI: Validation and application in alzheimer's disease," Neuroimage 13: 847-855 (2001).
Dale et al., "Cortical surface-based analysis. I. segmentation and surface reconstruction," Neuroimage 9: 179-194 (1996).
Dempster et al., "Maximum likelihood from incomplete data via the EM algorithm," Journal of the Royal Statistical Society. Series B (Methodological) 39: pp. 1-38 (1977).
Drury et al., "Computerized mappings of the cerebral cortex. A multiresolution flattening method and a surface-based coordinate system," J Cogn Neurosci 8: 1-28 (1996).
Dubes et al., "MRF model-based algorithms for image segmentation," Pattern Recognition, 1990 Proceedings, 10th International Conference on is 808-814 vol. 1 (1990).
Dupuis et al., "Variational problems on flows of diffeomorphisms for image matching," Quart. Appl. Math. 56: 587-600 (1998).
Duta et al., "Segmentation and interpretation of MR brain images: An improved active shape model," IEEE Trans Med Imaging 17: 1049-1062 (1998).
Evans et al., "Anatomical mapping of functional activation in stereotactic coordinate space," Neuroimage 1: 43-53 (1992).
Evans et al., "Brain templates and atlases," Neuroimage 62: 911-922 (2012).
Fischl et al., "Whole brain segmentation: Automated labeling of neuroanatomical structures in the human brain," Neuron 33: 341-355 (2002).
Fischl et al., "High-resolution intersubject averaging and a coordinate system for the cortical surface," Hum Brain Mapp 8: 272-284 (1999).
Fonov et al., "Unbiased average age-appropriate atlases for pediatric studies," Neuroimage 54: 313-327 (2011).
Grenander et al., "Computational anatomy: An emerging discipline," Q Appl Math LVI: 617-694 (1998).
Haller et al., "Three-dimensional hippocampal MR morphometry with high-dimensional transformation of a neuroanatomic atlas," Radiology 202: 504-510 (1997).
Hammers et al., "Automatic detection and quantification of hippocampal atrophy on MRI in temporal lobe epilepsy: A proof-of-principle study," Neuroimage 36: 38-47 (2007).
Han et al., "A topology preserving level set method for geometric deformable models," IEEE Transactions on Pattern Analysis and Machine Intelligence, 25: 755-768 (2003).
Heckemann et al., "Automatic anatomical brain MRI segmentation combining label propagation and decision fusion," Neuroimage 33: 115-126 (2006).
Held et al., "Markov random field segmentation of brain MR images," IEEE Trans Med Imaging 16: 878-886 (1997).
Hogan et al., "Mesial temporal sclerosis and temporal lobe epilepsy: MR imaging deformation-based segmentation of the hippocampus in five patients," Radiology 216: 291-297 (2000).
Holmes et al., "Enhancement of MR images using registration for signal averaging," J Comput Assist Tomogr 22: 324-333 (1998).

(56) References Cited

OTHER PUBLICATIONS

Jiang et al., "DtiStudio: Resource program for diffusion tensor computation and fiber bundle tracking," Comput Methods Programs Biomed 81: 106-116 (2006).
Klein et al., "Mindboggle: Automated brain labeling with multiple atlases," BMC Medical Imaging, Oct. 5, 2015, pp. 1-11.
Kittler et al., "On combining classifiers. Pattern Analysis and Machine Intelligence," IEEE Transactions on 20: 226-239 (1998).
Kittler et al., "Sum versus vote fusion in multiple classifier systems," Pattern Analysis and Machine Intelligence, IEEE Transactions on 25: 110-115 (2003).
Langerak et al., "Label fusion in atlas-based segmentation using a selective and iterative method for performance level estimation (SIMPLE)," Medical Imaging, IEEE Transactions on 29: 2000-2008 (2010).
Leung et al., "Automated cross-sectional and longitudinal hippocampal volume measurement in mild cognitive impairment and alzheimer's disease," Neuroimage 51: 1345-1359 (2010).
Lotjonen et al., "Fast and robust extraction of hippocampus from MR images for diagnostics of alzheimer's disease," Neuroimage 56: 185-196 (2011).
Lotjonen et al., "Fast and robust multi-atlas segmentation of brain magnetic resonance images," Neuroimage 49: 2352-2365 (2010).
Ma et al., "A bayesian generative model for surface template estimation," Int J Biomed Imaging 2010: 10.1155/2010/974957. Epub Sep. 20, 2010 (2010).
Ma et al., "Bayesian template estimation in computational anatomy," Neuroimage 42: 252-261 (2008).
Mazziotta et al., "A probabilistic atlas and reference system for the human brain," International consortium for brain mapping (ICBM) Philosophical Transactions of the Royal Society of London Series B: Biological Sciences 356: 1293-1322 (2001).
Mazziotta et al., "A probabilistic atlas of the human brain: Theory and rationale for its development," The International Consortium for Brain Mapping (ICBM). Neuroimage 2: 89-101 (1995).
Miller et al., "Geodesic shooting for computational anatomy," J Math Imaging Vis 24: 209-228 (2006).
Miller et al., "Group actions, homeomorphisms, and matching: A general framework," Int. J. Comput. Vision 41: 61-84 (2001).
Miller et al., "Mathematical textbook of deformable neuroanatomies," Proc Natl Acad Sci U S A 90: 11944-11948 (1993).
Miller et al., "On the metrics and euler-lagrange equations of computational anatomy," Annu Rev Biomed Eng 4: 375-405 (2002).
Mitchell et al., "Multistage hybrid active appearance model matching: Segmentation of left and right ventricles in cardiac MR images," IEEE Trans Med Imaging 20: 415-423 (2001).
Morey et al., "A comparison of automated segmentation and manual tracing for quantifying hippocampal and amygdala volumes," Neuroimage 45: 855-866 (2009).
Mori et al., "Stereotaxic white matter atlas based on diffusion tensor imaging in an ICBM template," Neuroimage 40: 570-582 (2008).
Mori et al., "MRI atlas of human white matter," Elsevier Science (Book Review) (2005).
Oishi et al., "Human brain white matter atlas: Identification and assignment of common anatomical structures in superficial white matter," Neuroimage 43: 447-457 (2008).
Paragios, "A level set approach for shape-driven segmentation and tracking of the left ventricle," IEEE Transactions on Medical Imaging, 22: 773-776 (2003).
Patenaude et al., "A bayesian model of shape and appearance for subcortical brain segmentation," Neuroimage 56: 907-922 (2011).
Pham et al., "Adaptive fuzzy segmentation of magnetic resonance images," IEEE Trans Med Imaging 18: 737-752 (1999).
Pohl et al., "A bayesian model for joint segmentation and registration," Neuroimage 31: 228-239 (2006).
Priebe et al., "Segmenting magnetic resonance images via hierarchical mixture modelling," Comput Stat Data Anal 50: 551-567 (2006).
Qin et al., "Gross feature recognition of Anatomical Images based on Atlas grid (GAIA): Incorporating the local discrepancy between an atlas and a target image to capture the features of anatomic brain MRI," NeuroImage: Clinical, vol. 3, pp. 202-221, Aug. 14, 2013.
Rex et al., "The LONI pipeline processing environment," Neuroimage 19: 1033-1048 (2003).
Rohlfing et al., "Evaluation of atlas selection strategies for atlas-based image segmentation with application to confocal microscopy images of bee brains," Neuroimage 21: 1428-1442 (2004).
Sabuncu et al., "A generative model for image segmentation based on label fusion. Medical Imaging," IEEE Transactions on 29: 1714-1729 (2010).
Shen et al., "An adaptive-focus statistical shape model for segmentation and shape modeling of 3-D brain structures," IEEE Trans Med Imaging 20: 257-270 (2001).
Tang et al., "Bayesian Parameter Estimation and Segmentation in the Multi-Atlas Random Orbit Model," PLOS One, vol. 8, Issue 6, Jun. 2013.
Tang et al., "Segmentation via multi-atlas LDDMM," Landman, B. A. & Warfield, S. K., eds. MICCAI 2012 Workshop on Multi-Atlas Labeling: 123-133 (2012).
Trouve, "An infinite dimensional group approach for physics based models," Technical Report. In Press (1995).
Tu et al., "Brain anatomical structure segmentation by hybrid discriminative/generative models," IEEE Trans Med Imaging 27: 495-508 (2008).
Vaillant et al., "Surface matching via currents," 3565: 1-5 (2005).
Van Essen, "A population-average, landmark- and surface-based (PALS) atlas of human cerebral cortex," Neuroimage 28: 635-662 (2005).
Van Campenhout et al., "Maximum entropy and conditional probability," IEEE Transactions on Information Theory, 27: 483-489 (1981).
Van Ginneken et al., "Active shape model segmentation with optimal features," IEEE Trans Med Imaging 21: 924-933 (2002).
Van Leemput et al., "A unifying framework for partial volume segmentation of brain MR images. Medical Imaging," IEEE Transactions on 22: 105-119 (2003).
Van Rikxoort et al., "Adaptive local multi-atlas segmentation: Application to the heart and the caudate nucleus," Med Image Anal 14: 39-49 (2010).
Verhoeven et al., "Construction of a stereotaxic DTI atlas with full diffusion tensor information for studying white matter maturation from childhood to adolescence using tractography-based segmentations," Hum Brain Mapp 31: 470-486 (2010).
Vese et al., "A multiphase level set framework for image segmentation using the mumford and shah model," International Journal of Computer Vision 50: 271-293 (2002).
Wakana et al., "Fiber tract-based atlas of human white matter anatomy," Radiology 230: 77-87 (2004).
Warfield et al., "Nonlinear registration and template driven segmentation," Brain Warping 4: 67-84. (1999).
Warfield et al., "Simultaneous truth and performance level estimation (STAPLE): An algorithm for the validation of image segmentation," IEEE Trans Med Imaging 23: 903-921 (2004).
Wells et al., "Adaptive segmentation of MRI data," Medical Imaging, IEEE Transactions on 15: 429-442 (1996).
Woolrich et al., "Bayesian analysis of neuroimaging data in FSL," Neuroimage 45: S173-86 (2009).
Yang et al., "3D image segmentation of deformable objects with joint shape-intensity prior models using level sets," Med Image Anal 8: 285-294 (2004).
Zhang et al., "Segmentation of brain MR images through a hidden markov random field model and the expectation-maximization algorithm," Medical Imaging, IEEE Transactions on 20: 45-57 (2001).

* cited by examiner

S110 – Receiving Imaging Data

S120 – Providing a Plurality of Atlases

S130 – Co-Registering the Plurality of Atlases to the Imaging Data

S140 – Assigning a Probability to Generate a Labeling Parameter

S150 – Classifying the Region of Interest

S160 – Suggesting an Anatomical Feature

Fig. 1A

AUTOMATED ANATOMICAL LABELING BY MULTI-CONTRAST DIFFEOMORPHIC PROBABILITY FUSION

CROSS REFERENCE TO RELATED APPLICATIONS

This is a national stage application under 35 U.S.C. § 371 of PCT/US2015/012092 filed Jan. 20, 2015 and this application claims priority to U.S. provisional application No. 61/928,772, filed Jan. 17, 2014, the entire contents of both are incorporated herein by reference in their entirety.

GOVERNMENT INTEREST

This invention was made with Government Support under grant Nos. RO1AG020012, R03EB04357, R01 DC011317; R01 EB000975, P41 EB015909, R01 EB008171, R01 HD065955, R21AG033774, and U01AG033655 awarded by the National Institutes of Health. The Government has certain rights in the invention.

TECHNICAL FIELD

The present invention relates to systems, methods and computer readable media for automated anatomical labeling.

BACKGROUND

The advent of high-resolution T1-weighted magnetic resonance (MR) neuroimaging technologies facilitates a detailed exploration into human brain anatomy. Quantitative studies have demonstrated that morphometric and functional responses of cortical and subcortical brain structures are highly correlated to numerous neuropsychiatric illnesses. There now exists a research community supported by universally deployed software packages [1-5] applying automated methods for reconstruction of the human brain structures, which often rely on pre-defined brain atlases. These atlases represent structural and functional information of the brain associated to single-subject, population-averaged, or multiple brain atlas coordinate systems including whole brain based coordinate systems [6-11], white matter based coordinate systems [12-17], and surface based coordinate systems [18-21]; see [22] for an excellent review. Often these are coupled with global deformable template methods, small and large deformation in nature [23-38], for transferring information across anatomical coordinate systems.

In these deformable template approaches, the solutions inherit the smoothness and the topological properties from the atlas. A problem focused on in this disclosure is to extend the generative random diffeomorphic orbit model that has been used in single atlas approaches [30,31,35,39] to the multiple atlas model, in which not only are the diffeomorphic changes in coordinates unknown but also jointly measurable parameters are unknown such as those arising in: (1) atlas labeling corresponding to disease inference, (2) structure parameters such as volumes, or (3) dense label field estimation associated with segmenting the target image into anatomically defined regions. In all the three examples, the atlas in the collection is unknown in generating the image, implying the posterior distribution is multi-modal determined by the multiple atlases. In these global deformable template methods [40], the parameters to be estimated are not "isolated" from the simultaneous acquisition of the global shape phenotype, which is encoded via the structure of the template and the associated deformation.

Since the atlases used for interpreting the image are not known, the conditional-mean technology of the expectation-maximization (EM) algorithm [41] underlies the problem.

Thus there remains a need for improved automated segmentation systems, methods and devices.

SUMMARY

In one aspect of the invention, a computer-implemented method for classifying a region of interest of a subject includes receiving imaging data comprising at least one image element, the imaging data comprising the region of interest of the subject; providing a plurality of atlases, each of the plurality of atlases having a candidate region that corresponds to the region of interest of the imaging data, each of the plurality of atlases having at least one image element with associated location and property information; co-registering the plurality of atlases to the imaging data, using at least one processor; assigning a probability to generate a labeling parameter for the region of interest, the probability being associated with each atlas; and classifying the region of interest of the subject based on the assigning.

In another aspect of the invention, a system for classifying a region of interest of a subject includes a memory storing computer-executable instructions; and a processor that is coupled to the memory and that is configured to execute the computer-executable instructions to perform: receiving imaging data comprising at least one image element, the imaging data comprising the region of interest of the subject; providing a plurality of atlases, each of the plurality of atlases having a candidate region that corresponds to the region of interest of the imaging data, each of the plurality of atlases having at least one image element with associated location and property information; co-registering the plurality of atlases to the imaging data; assigning a probability to generate a labeling parameter for the region of interest, the probability being associated with each atlas; and classifying the region of interest of the subject based on the assigning.

In another aspect of the invention, a non-transitory computer readable storage medium for classifying a region of interest of a subject, includes instructions that when executed enable a computing system to perform: receiving imaging data comprising at least one image element, the imaging data comprising the region of interest of the subject; providing a plurality of atlases, each of the plurality of atlases having a candidate region that corresponds to the region of interest of the imaging data, each of the plurality of atlases having at least one image element with associated location and property information; co-registering the plurality of atlases to the imaging data, using at least one processor; assigning a probability to generate a labeling parameter for the region of interest, the probability being associated with each atlas; and classifying the region of interest of the subject based on the assigning.

Additional features, advantages, and embodiments of the invention are set forth or apparent from consideration of the following detailed description, drawings and claims. Moreover, it is to be understood that both the foregoing summary of the invention and the following detailed description are examples and are intended to provide further explanation without limiting the scope of the invention as claimed.

BRIEF DESCRIPTION OF THE DRAWINGS

FIG. 1A shows a flowchart of one embodiment of the invention.

DETAILED DESCRIPTION

Figure 1B:
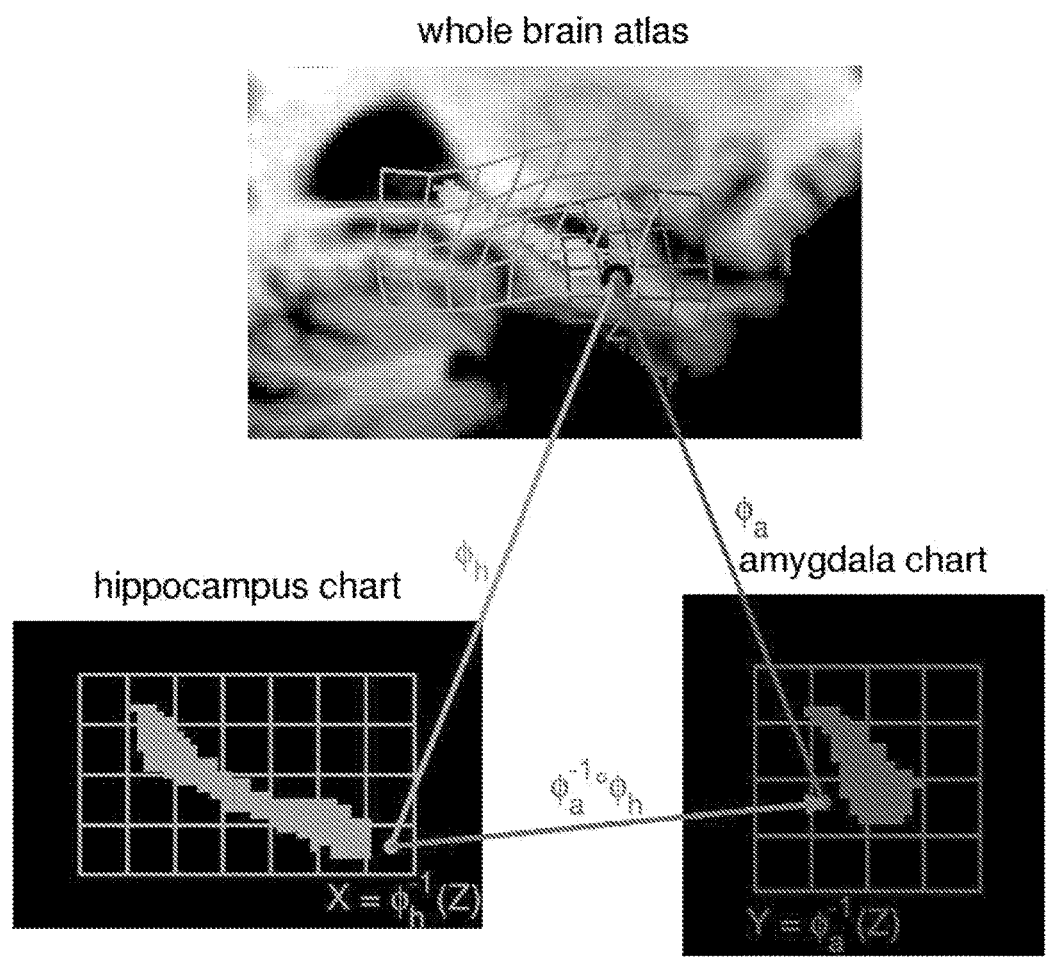
FIG. 1B shows a depiction of two charts and the associated diffeomorphisms chosen to illustrate the interpretation, according to one embodiment of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

FIG. 1A shows a computer-implemented method for classifying a region of interest of a subject. In one embodiment, the method can include receiving S110 imaging data that includes at least one image element and the region of interest of the subject. The at least one image element can be at least one of a pixel, a plurality of pixels, a voxel, or a plurality of voxels. The imaging data can be generated from at least one of magnetic resonance imaging (MRI), computed tomography (CT), positron emission tomography (PET), ultrasound, or nuclear tracer three-dimensional imaging. The region of interest can include a portion of at least one of a brain, a heart, a liver, skin, a lung, another organ, one or more bones, or any combination thereof.

The method can include providing S120 a plurality of atlases where each of the plurality of atlases have a candidate region that corresponds to the region of interest of the imaging data. Each of the plurality of atlases can have at least one image element with associated location and property information. The method can include co-registering S130 the plurality of atlases to the imaging data, using at least one processor. The method can include assigning S140 a probability to generate a labeling parameter for the region of interest, where the probability can be associated with each atlas. The method can also include classifying S150 the region of interest of the subject based on the assigning step. The probability used can meet a predetermined statistical significance in the classifying step S150.

In one embodiment, the probability for the labeling parameter can be based on a plurality of probability terms of each atlas. The plurality of probability terms can include a location value and a property value of the at least one image element of each atlas. The property value of the at least one image element can be intensity. The classifying step can include using a predetermined formula to combine the plurality of probability terms, as explained in the examples section. In one embodiment, the location value can be selected from a most probable location assignment among the plurality of atlases and the property value can be selected from a most probable intensity assignment from the plurality of atlases.

In one embodiment, the co-registering S130 the plurality of atlases can generate a mixture of probabilities from each atlas of at least one labeling parameter. The generated mixture of probabilities can be maximized with respect to the parameter being estimated, and the mixture can be generated via superposition and weighting of the probability from each atlas. The generated mixture can be used in generating the labeling parameter. The probability terms can be generated from statistical noise modeling of an observed imager modality of the imaging data. The statistical noise model can determine the location values and the property values.

The labeling parameter can be one or more of a number of parameters that can be analyzed, for example, a size of tissue of the region of interest of the subject, an amount of cerebrospinal fluid of the region of interest, a type of tissue of the region of interest of the subject, etc.

For each of the atlases, the classifying step can incorporate a weight corresponding to a function of a modality of the imaging data and the atlas. The modality of the imaging data and the atlas can be T1-weighted imagery. Other modalities are also contemplated within the scope of one embodiment of the present invention, such as T2-weighted and diffusion. Thus, the weight can correspond to a function of at least two modalities of the imaging data and the plurality of atlases. The weight can increase as a difference in intensity between the region of interest and the corresponding candidate region of the atlas decreases. The weight can be determined using an expectation-maximization algorithm.

The function of the modality can be determined by an MRI target image modality, a measure of intensity, a vector of intensities, a matrix of intensities, or a finite alphabet valued label such as a semantic label arising from an ontology and atlas image intensity and/or a vector or a matrix of intensities and/or a finite alphabet valued label such as a semantic label arising from the ontology. The imaging data can include a plurality of images and the receiving step can include receiving the plurality of images. While in one embodiment the co-registering step S130 can include co-registering the plurality of atlases to a single image, in another embodiment the co-registering step can include co-registering the plurality of atlases to a plurality of images. The measure of intensity can be measured in a variety of ways including, for example, a mean intensity of the region of interest; a sum of intensities of the region of interest; a highest intensity of the region of interest; a lowest intensity of the region of interest; a vector or a matrix of any of these values; and a finite alphabet semantic labeling from an ontology.

In one embodiment, for each of the plurality of atlases, the classifying step S150 can incorporate a weight corresponding to a function of deformation of the image element from being mapped to the atlas. In this embodiment, the weight can increase as an amount of deformation of the region of interest from being mapped to the atlas decreases. The weight can also be a function of other features that are predetermined between the imaging data and the atlas. For example, the other features can include non-image information of the subject and atlases. The non-image information can include a function of an age of the subject of the imaging data and an age corresponding to the plurality of atlases and/or a diagnosis of the subject of the imaging data and a diagnosis corresponding to the plurality of atlases.

For each of the plurality of atlases, the classifying step S150 can incorporate global anatomical features in the image such as a size of the brain and ventricles or intensities of the brain and non-brain tissues.

At least one of the plurality of atlases can be co-registered to the imaging data using a linear transformation, a nonlinear transformation, and/or a diffeomorphic transformation.

The method can further include suggesting S160 that the subject has an anatomical feature based on the classifying step S150. The anatomical feature can be at least one of an abnormality, a disease, a condition, a diagnosis, or any combination thereof.

A difference in intensities between the candidate regions of interest of the plurality of atlases and the region of interest of the imaging data can be determined by determining a distance vector.

In one embodiment, the co-registering of atlases can generate a mixture via superposition and weighting of the probability from each atlas of any of the parameters to be estimated (e.g., size, amount of gray matter, cerebrospinal fluid (CSF), etc.) from which the most likely parameters being estimated can be generated by maximizing the mixture of probabilities with respect to those parameters being estimated. Further, the multiple probability terms can be generated from standard statistical noise modelling of the observed imager modality (e.g., MRI, CT, PET) including, but not limited to, linear and non-linear functions of the image-based features such as location values (coordinates) and voxel properties such as voxel intensity determined by the statistical noise model representing the imaging modality.

In one embodiment, each atlas can define at least one structure. Through co-registering the atlases to the subject imaging data, the atlases can cast their opinion about where the structure is into the subject imaging data. Once the multiple atlases provide potentially different locations of the structure, a label fusion can take place, which merges the opinions of the multiple atlases and come to one opinion. One approach is by majority voting; that is, if a majority of the atlases indicate a particular voxel is outside the structure, then this voxel is not labeled as that structure. On the other hand, if a majority of the atlases say that the voxel is the structure, the voxel can be labeled as such.

Next, voxel property information, such as intensity information, can be applied. For example, if all the atlases indicate that the structure is darker than surrounding non-structure voxels, this information can be incorporated. Thus, even if a majority atlases under location information indicate that the voxel is a particular structure, if the voxel is bright, it may not be the structure. Likewise, even if a minority of the atlases indicate that the voxel is a particular structure, if the voxel is dark, it could be the structure.

Thus, one embodiment of the invention can provide a framework for incorporating the probability that the image element is a particular structure based on location and the probability that the image element is a particular structure based on intensity using a formula that formally integrates these two terms in a rigorous mathematical manner. Because of the solution, the probability terms can be any number of fields related to the image or can be non-image fields. For example, ages that correspond to the atlases can be applied. Thus, if the subject is 80 years old, a 20-year old atlas can indicate that a voxel is a particular structure and an 85-year-old atlas can indicate that the voxel is not the structure, then the 85-year-old atlas can get more weighting. Further, diagnosis information can be applied. For example, if the subject is suspected of Alzheimer's disease, then we can weight atlases with Alzheimer's disease more. Also, different imaging modalities can be incorporated. Thus, one embodiment of the present invention provides for a unified solution for one to integrate more than two information terms (e.g., probability) about whether this voxel is a particular structure or not.

The conditional-mean can explicate the weights with which the atlases contribute to the interpretation of the image in the multi-modal representation. In this setting, there can be a likelihood indexed over each atlas which can then be combined via superposition to generate the single a posteriori distribution that the Bayes maximum a posteriori (MAP) estimator optimizes. The superposed weights can be the conditional expectations of the latent variables determining the amount that each atlas-specific likelihood is factored into the single a posteriori likelihood. We name this the likelihood-fusion equation.

A significant extension, developed in this disclosure, of the random atlas model is to add to the global deformable template the notion of locality which is usually associated to the local approaches from differential geometry [42]. Here an atlas can be defined as collections of local charts linked through diffeomorphic coordinate transformations. The anatomical model can construct the atlas via charts of subcortical and cortical volumes delineated in varying anatomical coordinate systems. In one embodiment, we focus on sub-cortical structures and the ventricles. The MAP problem labels each voxel of the target image via mixtures of the locally-chart-defined conditional a posteriori probabilities. Since for any voxel, a chart from any of the atlases could be the generator of its mean field and the associated conditional a posteriori probability, the conditional-mean of the latent variables on chart selection can be calculated for each voxel in the target image, thus providing locality in the segmentation as part of the global model.

The multi-atlas random orbit model used here for segmentation differs from several other approaches in the following ways. First, the proposed method can solve for the single set of unknown segmentation variables W and conditions only on the observable image I. It does not generate a set of segmentation labels associated to each atlas-chart interpretation, which might then be combined via voting for fusing based on a performance metric [37,43-49]. The conditional expectation framework derived here can explicate the role of each chart and atlas by averaging via the conditional-expectation over the atlas-dependent log-likelihoods generating the single fused likelihood, from which the segmentation labels are generated as maximizers. This is likelihood-fusion instead of label-fusion.

Also, it is noteworthy that, in the likelihood-fusion approach, we do not generally find that the posterior probability is concentrated as a delta-function supported on one or a small number of the same atlases, which would be equivalent to the generalized likelihood problem in which the atlases and charts are tested separately with the "closest" ones determining the solution via combination as in [45,49-51]. The fact that the convex combination of atlases is rarely concentrated on a single or a small subset of atlases implies that the likelihood-fusion can mediate the high dimensionality of atlas selection which the generalized likelihood problem would suffer from. The likelihood-fusion is associated to averaging of log-probabilities over multiple atlases.

A method proposed here can be a generative model approach. See [52]. The generative model can extend the conditionally random field orbit model of Computational Anatomy (CA) to the multiple-atlas case, modeling the images as conditionally random fields conditioned on the random segmentation field and the random unknown atlas charts to be selected. Chart selection is applied throughout the field, extending the global nature of diffeomorphic methods to local selection via spatial chart selection throughout the random field.

In this disclosure, we investigate the quality of the multi-atlas multi-chart diffeomorphic orbit model for the segmentation of deep gray matter structures, as well as the ventricles, using T1-weighted MR images. We were particularly interested in characterizing brain atrophy, and therefore, we tested our method in elderly and dementia populations. Results from the automated segmentation scheme have been compared with the manual segmentations to examine the accuracy of the method. More specifically, we investigate: 1) the level of accuracy we can achieve using a single-atlas approach; 2) the degree of improvement by incorporating the multi-atlas approach; and 3) the impact of the anatomical variability on accuracy based on a normal elderly and a dementia patient population.

In FIG. 1B, the charts are related via diffeomorphic coordinate transformations as depicted in the figure, in which points X, Y in the hippocampus chart and the amygdala chart are compared using the forward and inverse mappings. The charts can be manually delineated structures including the amygdala, caudate, hippocampus, putamen, thalamus, lateral ventricle, the 3rd ventricle, and the 4th ventricle.

EXAMPLES

2.1 Atlas Selection and the Random Orbit Model

We first examine the class of maximum a posteriori problems in which the generalized parameters $\theta$ are jointly distributed with respect to the observed MRI image $I$ in the context of a family of atlases $\{I^a\}$. The parameters can take several forms—the disease type associated to the image, the volume of a structure in the image, or the labeling of the image into a segmentation field of subcortical structures. The likelihood model for inference based on a single atlas $a$ is the form of a conditional density jointly measured with the unknown parameters $p(I, \theta|a)$. Viewing the multiple-atlas problem with atlas $A$ random, the fusion of the likelihood functions gives the multi-modal mixture model:

$$p(I, \theta) = \sum_a p(I, \theta \mid A = a)\pi_A(a), \quad (1)$$

with $\pi_A(a)$ the prior averaging over atlases. This is the generative model with which we can score each image and perform inference on the parameters within our multi-modal model.

2.1.1 The Random Orbit Model.

Scoring the images in Eq. (1) can boil down to the calculation of the conditional density of the image given any particular atlas $p(I|a)$. For this, we use the generative random orbit model to model the image as a random field [31], a noisy observation of an unknown change in coordinates $\varphi$ of the underlying atlases $I^a$, $a=1, \ldots$ which generate it. Conditioned on the atlas as well as the diffeomorphism, the observed image has a conditional density indexed over the voxel lattice $p(I|I^a \bigcirc \varphi, a) \sim \exp[-\frac{1}{2}\|I-I^a \bigcirc \varphi\|^2]$, with the diffeomorphisms generated via flows $$\varphi = \int_0^1 v_t(\varphi_t)dt, v \in V.$$

We can use the shorthand notation for the density $p(I|\varphi, a)$.

The diffeomorphic flows can be generated by the set of time-indexed vector fields $\dot{\varphi}_t = v(\varphi_t)$ with finite integrated norm $$\left\{ v : \int_0^1 \|v_t\|_V \, dt < \infty \right\}.$$

The flows can be spatially smooth since time-sections of the vector fields are of finite norm $\|v_t\|_V$ dominating a Sobelev norm of spatial derivatives existing in squared error [30]. For computational purpose, we use an operator-induced norm so that $$\|f\|_V^2 = \sum_{i=1}^{3} \|Lf_i\|_2^2 \text{ and } \|f_i\|_2^2 = \int |f_i(x)|^2 dx$$

dx with the differential operator $L=-\beta \nabla^{2p}+\gamma$, where $\nabla^{2p}$ is the Laplacian operator with power $p \geq 1.5$, and $\beta$, $\gamma$ are real numbers. The prior in the random diffeomorphism orbit model is built using the geodesic energy in the space of diffeomorphisms $\dot{\varphi}^v = v(\varphi^v)$ relative to the identity mapping, privileging the initial tangent vector determining the geodesic $\pi(\varphi^{v_0}|a) \sim \exp(-c\rho_a^2(\mathrm{id},\varphi^{v_0}))$ with $\rho_a^2(\mathrm{id},\varphi^{v_0})=\exp(-c\|v_0\|_V^2)$. In the random orbit model, the conditional density of the image is computed via the nuisance integral:

$$p(I|a)=\int p(I,\varphi|a)d\varphi=\int p(I|\varphi,a)\pi(\varphi|a)d\varphi. \quad (2)$$

2.1.2 Atlas Selection for Real-Valued MAP Estimation.

Model selection can play a fundamental role in the MAP estimation of parameters. We can associate the high dimensional parameter set $\theta \in R^N$ to the MRI $(I,\theta)$. At the heart of the MAP estimation problem is how much each single atlas contributes to interpreting the image jointly with its parameters, denoted as the conditional probability according to $P_A(a|I,\theta)$. We use the EM algorithm to find the MAP estimator $\theta$. The following disclosure shows a proof that the EM algorithm is monotonic in likelihood for the sequence of segmentation labels and that fixed points satisfy the necessary conditions of being a MAP estimator.

Statement:
Given the maximum a posteriori (MAP) problem $$\max_{W=W_1,\ldots,W_N} \sum_a p(I, W \mid a)\pi(a), \quad (1)$$

then the mapping $W^{old} \to W^{new}$ with atlas selector $P_A(a \mid I, W^{old})$, associated to iteration $$W^{new} = \arg\max_W \sum_a P_A(a \mid I, W^{old})\log p(I, W \mid a), \quad (2)$$

has fixed points maximizing Eq. (1) and is monotonically increasing in likelihood with $$\sum_a p(I, W^{new} \mid a)\pi(a) \geq \sum_a p(I, W^{old} \mid a)\pi(a). \quad (3)$$

Proof:
Maximizing (2) with respect to parameters $\theta=W$ and evaluating at fixed points, $W^{old}=W^{new}=W^*$ gives, $$0 = \partial_W \sum_a P_A(a \mid I, W^{old})\log p(I, W \mid a)\mid_{W^*} \quad (4)$$

$$= \sum_a \frac{p(I, W^{old} \mid a)}{p(I, W^{old})}\pi(a)\frac{\partial_W p(I, W \mid a)}{p(I, W \mid a)}\mid_{W^*}$$

$$= \sum_a \frac{\partial_W p(I, W^* \mid a)}{p(I, W^*)}\pi(a).$$

The monotonicity is proven showing it is an EM algorithm [41]. The image augmented with unknown atlas labelings is the complete-data (I, A) with incomplete-data the MRI observable I, and the many-to-one map $h:(I, A) \to I$ discards the labels. The atlases generating the image voxels are not observable; the conditional expectations of the indicator functions determine how to fuse the likelihood interpretation associated to each atlas. Introducing the indicator function $\delta_A(a)=1$ means atlas A=a generates the image, the density conditioned on the complete-data atlas labels is given by $$p(I, W \mid A) = \prod_a p(I, W \mid a)^{\delta_A(a)}. \quad (5)$$

Computing the logarithm and taking the conditional mean expectation of the complete-data log-likelihood gives the weighting of the log-likelihood $$E\{\log p(I, W) \mid I, W^{old}\} = \sum_a E\{1_A(a) \mid I, W^{old}\}\log p(I, W \mid a) \quad (6)$$

$$= \sum_a P_A(A=a \mid I, W^{old})\log p(I, W \mid a),$$

where we have used $E\{1_A(a) \mid I, W^{old}\} = P_A(a \mid I, W^{old})$ proving the iteration. The monotonicity is proved using the properties of EM Algorithms. Define the complete-data X=(I, A) and its likelihood $f(X;\theta)$ given by Eq. (5); the incomplete-data is denoted as Y=I with likelihood $g(Y;\theta)$ of Eq. (1). The many-to-one map discards the labels so that the likelihoods transform according to $$g(Y; \theta) = \int_{\{X: h(X)=Y\}} f(X; \theta)dX.$$

Denoting the conditional density as $$k(X \mid Y; \theta) = \frac{f(X; \theta)}{g(Y; \theta)},$$

then 1-step of the mapping gives:

$$E_{Y,\theta^{old}}\log\frac{f(X; \theta^{old})}{k(X \mid Y; \theta^{old})} \leq E_{Y,\theta^{old}}\log\frac{f(X; \theta^{new})}{k(X \mid Y; \theta^{old})} \leq \quad (7)$$

$$\max_p \int_{\{X: h(X)=Y\}} p(X)\log\frac{f(X; \theta^{new})}{p(X)}dx.$$

The cross-entropy maximizer can be given by the tilted distribution $$\hat{p}(X) = \frac{f(X; \theta^{new})}{g(Y; \theta^{new})}$$

introduced by [89]. Since this is the conditional density, the left and right hand sides of Eq. (7) are none other than the incomplete data log-likelihoods giving log $g(Y;\theta^{old}) \leq$ log $g(Y;\theta^{new})$.

2.2 The Hierarchical Segmentation Random Orbit Model

Now we examine MAP estimation in the high-dimensional setting of unknown segmentation fields, $\theta=W_1, \ldots, W_N$ corresponding to subcortical labelings $W_i \in \{A, C, H, T, \ldots\}$ of amygdala, caudate, hippocampus, thalamus . . . , associated to the MRI (I, $\theta$)=($I_1, W_1, \ldots, I_N, W_N$) indexed over the voxel lattice of size $N=n^3$.

We define a hierarchical model between the image and the underlying diffeomorphic change in coordinates of the atlas, so that W splits the target image and the diffeomorphic change of coordinates. Conditioned on W, the joint measurement I, $\varphi$ is independent with the image being a conditionally independent random field from voxel to voxel under the product distribution:

$$p(I, W \mid a, \varphi) = p(I \mid W, a, \varphi)p(W \mid a, \varphi) \quad (3)$$

$$= \Pi_i p(I_i \mid a, W_i)p(W \mid a, \varphi).$$

The term $p(I_i \mid a, W_i)$ can be computed using Gaussian mixture models. The probability $p(W_i \mid a, \varphi)$ is calculated by transferring the segmentations of the atlas under the action of the diffeomorphism between the atlas and the target. For voxel $x_i$ corresponding to atlas coordinate $\varphi_a^{-1}(x_i)$ which is interior to the atlas anatomical labels so that all neighbors on the lattice are of the same label type, no interpolation is required and the prior probability is an indicator function; otherwise the probability can be interpolated. To compute the joint probability of image and segmentation labeling I, W for the iterative MAP algorithm, we must solve the integral over the nuisance variables of coordinate transformations for which we use the mode approximation $\varphi^W = \arg\max_\varphi p(W|a, \varphi)\pi(\varphi|a)$ approximating $$p(I,W|a) = \int p(I,W|a,\varphi)\pi(\varphi|a)d\varphi \sim p(I,W,\varphi^W|a), \quad (4)$$

with $\pi(\varphi|a)$ the prior on transformations conditioned on the atlas.

2.2.1 Local Charts

Locality is introduced into the global representations by defining the atlases to correspond to manually-labeled T1-weighted imagery with empirical mean and standard-deviation parameters obtained over the subcortical structures indexed throughout the volume. The charts are collections of the manually delineated sixteen subcortical and ventricular structures, each with means and variances; associated to each chart are the parameters $\mu_a$, $\sigma_a$ representing the structure. Locality of the atlas-charts is introduced by indexing to the target image the atlas label field $A = (A_1, A_2, \ldots)$, where $A_i$ denotes the atlas-chart interpreting the target voxels.

The charts are "open sets" containing each of the subcortical structure so that their unions cover the full volume and are related with each other as depicted in FIG. 1 via diffeomorphic coordinate transformations. Two points X and Y in the hippocampus chart and the amygdala chart may be compared using the forward and inverse mappings via: $Y = \varphi_a^{-1} \circ \varphi_h(X)$, $X = \varphi_h^{-1} \circ \varphi_a(Y)$. This ensures that during segmentation, multiple charts overlapping allows for weighted interpretation, since all "mediation" of errors occurs at the boundaries of the structures. At one boundary of the hippocampus, for example, are portions of the ventricles, at another the amygdala. Interpretation of those boundary voxels is supported by multiple charts which can overlap and therefore may offer alternative contributions.

The multi-atlas random orbit model of the observed imagery I is that the mean-fields are random deformations of atlas-charts arising from perhaps different atlases, each locally indexing different parts of the brain. The image and diffeomorphism are linked through the fact that the diffeomorphism determines the segmentation. The image is conditionally Gaussian with mean determined by the deformed atlas-chart according to $I_i = \mu_a(W \circ \varphi_a^{-1}(x_i)) + \text{noise}$, with the noise being additive Gaussian. This indexing of every point in the target image with a chart label gives the locality. The probabilistic structure we induce corresponds to splitting the image and diffeomorphism so that, given the segmentation, the image is conditionally independent of the diffeomorphism $$p(I_i | W_i, \varphi, a) = p(I_i | W_i, a) \sim \exp\left(-\frac{(I_i - \mu_a(W_i))^2}{2\sigma_a(W_i)^2}\right).$$

We also use Gaussian mixture models for the conditional random field as introduced in [53].

2.2.2 Likelihood Fusion and the EM Algorithm

We introduce the localized indicator functions associated to the atlas field labelling $A = (A_1, A_2, \ldots)$ with $\delta_a(A_i) = 1$ meaning that atlas $A_i = a$ is used to interpret the image I; the joint density is conditionally independent between different voxels, conditioned on the atlas-chart labels given by $$p(I, W | A = A_1, A_2 \ldots) = \prod_i \prod_{a_i} p(I, W | a_i)^{\delta_{a_i}(A_i)}, \quad (5)$$

where $a_i$ designates the atlas used to interpret the image voxels. For the case where the atlases are global, then one atlas is used to interpret the image; for all of the cases shown here the atlas-charts are locally defined subcortical structures with multiple atlas-charts interpreting each image.

The Algorithm:

Define the Q-function as the conditional expectation of the complete-data log-likelihood according to $$Q(W; W^{old}) = E\{\log p(I, W | A) | I, W^{old}\} \quad (6)$$

$$= \sum_i \sum_a P_{A_i}(a | I, W^{old})\log p(I, W | a).$$

Then the sequence of iterates $W^{(1)}, W^{(2)}, \ldots$, associated to the alternating maximization defined by the iteration:

$$W^{new} = \arg\max_W Q(W; W_{old}), \quad (7)$$

is monotonic in the incomplete-data likelihood (proven in Appendix) with atlas selector $P_{A_i}(a|I, W^{old})$. The monotonicity follows from the fact that Eq. (6) is an EM Algorithm, as proven in the Appendix, since $$Q(W; W^{old}) = E_{P_A(\cdot|I, W^{old})}\{\log p(I, W | A) | I, W^{old}\}$$

$$= E_{P_A(\cdot|I, W^{old})}\left\{\sum_i \sum_a \delta_a(A_i)\log p(I, W | a)\right\}$$

with Eq. (6) following from the expectation $E_{P_A(\cdot|I, W^{old})}\delta_a(A_i) = P_{A_i}(a|I, W^{old})$. Eq. (6) is the likelihood-fusion equation. During the iteration, the sequence of conditional probabilities $P_{A_i}(\cdot|I, W^{old})$ derived from the conditional mean of the indicator functions encodes the set of atlases being selected in the interpretation of any particular voxel. Computing the maximization requires calculating the integral over the nuisance of coordinate transformation for which we use the mode approximation. The general steps of the algorithm can be summarized as follows:

1. Initialize: $W^{old}$, and $\varphi^{old}$ for each atlas, $P_{A_i}(a) = $ uniform
2. Compute optimized mappings $$\varphi^{old} = \arg\max_\varphi p(W^{old}|a, \varphi)\pi(\varphi|a) \quad (8)$$

3. Compute the approximated atlas selector $$\hat{P}_{A_i}(a | I, W^{old}) = \frac{p(a, \varphi^{old} | I, W^{old})}{\sum_a p(a, \varphi^{old} | I, W^{old})} = \frac{p(I, W^{old}, \varphi^{old} | a)\pi(a)}{\sum_a p(I, W^{old}, \varphi^{old} | a)\pi(a)} \quad (9)$$

4. Generate new segmentation $W_i^{new}$, i=1, ..., n maximizing approximate Q-function $$\max_W \hat{Q}(W; W^{old}) = \sum_i \sum_a \hat{P}_{A_i}(a | I, W^{old})\log p(I, W, \varphi^W | a). \quad (10)$$

5. If either $\|W^{new}-W^{old}\|^2 < \varepsilon$ or total iterations is bigger than 100, then stop, otherwise, update segmentation, $W^{old} \leftarrow W^{new}$, and go to 2.

Remark.

To maximize Eq. (10), we iterate between fixing the diffeomorphism and maximizing the segmentation, then locally maximizing the diffeomorphisms for the fixed segmentation labeling using Eq. (4) to define log p(I, W, $\varphi_W$|a). Locality is implied here since for atlas-charts, only segmentation labels in the target image in the vicinity of the atlas-chart are determined by the log-probability.

To maximize Eq. (8), we use measures of the distance between the segmentation $W^{old}$ of the target structures and the diffeomorphic mapping results from the template structures to the target, analogous to the Large Deformation Diffeomorphic Metric Mapping (LDDMM) for image matching and surface matching. We have examined several approaches for computational purposes. The first computes the distance between the atlas structure and the structures in $W^{old}$ via dense LDDMM image matching [54]. Given the pair ($W^{old}$, $W^a$), both of which are viewed as dense functions over the image domain, the vector field is generated to minimize the energy $$E(v) = \int_0^1 \|v_t\|_V^2 \, dt + \frac{1}{\sigma^2} \|W^a \circ \varphi^{-1} - W^{old}\|_2^2. \quad (11)$$

The LDDMM variational problem has direct interpretation as a MAP estimator. Associate to $\varphi^v$ is the initial momentum or the initial vector field [55] since it satisfies the ordinary differential equation $\dot{\varphi}^v = v(\varphi^v)$. The smooth norm $\|\cdot\|_V^2$ on the spatial derivatives of the velocity field is chosen via the Laplacian smoothness operator based on parameters $\alpha$ and $\gamma$, for which we use a ratio-cascading method as described in [56]; the ratio $\alpha/\gamma$ is gradually decreased to improve numerical stability and prevent sub-optimal local minima.

In a second embodiment, a method we use to compute the distance is to create triangular meshes of the structures and compute the distance between the atlas structures and meshes of the structures in $W^{old}$ via LDDMM surface matching [57]. The third method for computing distance is to compute the overlap via set distance calculations which is extremely fast for determining p($W^{old}$|a, $\varphi$); the Dice overlap is one example. For the prior probability $\pi$(a, $\varphi$), we weigh solutions via the metric distance in diffeomorphism space given by the exponential of geodesic length.

For computational purpose, we remove outlier atlases used in the computation following a robust scoring scheme. See [48]. For each conditional probability representing the overlap p($W^{old}$|a, $\varphi$), we calculate the mean $\bar{p}$ and remove atlases that are 2$\sigma$ outliers:

$$\hat{P}_{A_i}(a \mid I, W^{old}) = \frac{p(a_i, \hat{\varphi} \mid W^{old}, I) 1_{<\bar{p} \pm 2\sigma}(p)}{\sum_a p(a, \hat{\varphi} \mid W^{old}, I) 1_{<\bar{p} \pm 2\sigma}(p)}. \quad (12)$$

2.3 Subcortical Structure Segmentation

In this study, sixteen deep gray matter and ventricles structures were manually defined in the atlases images, which cover only a small part of the images. We defined a cuboid region of interest (ROI) encompassing all the structures of interest in all atlases, and modeled the segmentations within this ROI. Voxels inside the ROI not belonging to any of the sixteen manually delineated structures can be automatically labeled as white matter, gray matter, or cerebrospinal fluid (CSF) based on a local brain tissue segmentation algorithm [53]. This generic labeling of tissues outside the sixteen structures of interest ensures that all voxels were labeled. Because the likelihood-fusion algorithm tries to assign a label with the highest probability to each voxel, this type of "generic" labels outside the structures of interest (in this case, the 16 manually segmented structures) can be necessary to avoid over assignment.

2.3.1 Subject Data and Comparison Metrics.

In this study, we use T1-weighted images from 35 subjects from three groups, as described in Table 1. Magnetization Prepared Rapid Gradient Recalled Echo (MPRAGE) T1-WIs (TR/TE=8.4/3.9 ms) were acquired using 3T whole-body MRI scanners (Philips Medical Systems, Best, The Netherlands), with an axial orientation and an image matrix of 256×256. Participants were scanned with two slightly different protocols: one used a field of view (FOV) of 230×230 mm and 120 slices of 1 mm thickness; and the other used an FOV of 240×240 min and 140 slices of 1.2 mm thickness. These images were then manually segmented into sixteen structures—left and right hippocampus, amygdala, caudate, putamen, pallidum, lateral ventricle, thalamus, the $3^{rd}$ ventricle, and the $4^{th}$ ventricle.

To quantitatively evaluate the accuracy of one embodiment of the invention, we employed a leave-one-out cross-validation method on the datasets of Group 1 and Group 2. For Group 3, we used datasets from Group 1 and Group 2 as the atlases for segmentation. Manual segmentations were regarded as the gold standard. The segmentation accuracy was measured through the use of the Dice overlap coefficients. The Dice overlap is computed as:

$$D = \frac{2TP}{2TP + FP + FN},$$

where TP, true positive, is the volume of the region that belongs to both the automated segmentation and the manual segmentation, FP, false positive, is the volume of the region that belongs to the automated segmentation but not the manual segmentation, and FN, false negative, is the volume of the region that belongs to the manual segmentation but not the automated segmentation.

Ethics Statement

All subjects provided written consent for participation in accordance under the oversight of the Johns Hopkins Medicine Institutional Review Board (JHM-IRB). Additionally, for those subjects with dementia, the consent form was co-signed by a family member. The Johns Hopkins Institutional Review Board approved this study.

2.3.2 Comparison with Label-Fusion Methods

The segmentation accuracy of the proposed method was compared with that of the segmentations obtained from two label-fusion techniques: STAPLE [12] and Spatial STAPLE [58]. STAPLE and Spatial STAPLE were chosen for the comparison because they provide state-of-art segmentation accuracy and are widely used for multi-atlas label-fusion based segmentations. For a comparison, the multi-atlas LDDMM likelihood-fusion method was compared with STAPLE and Spatial STAPLE by using the codes which were available via the "MASI Label Fusion" project [58] on the NeuroImaging Informatics Tools and Resources Clearinghouse. The parameters for STAPLE and Spatial STAPLE were optimized through the consultation from Simon Warfield (STAPLE) and Bennett Landman (Spatial STAPLE). For both algorithms, we used the log-odds of the majority voting results as the explicit spatically-varing prior. The convergence factor was chosen to be $1 \times e^{-4}$. The EM algorithm for both STAPLE and Spatial STAPLE was designed to start with an initial estimate of the label probabilities, instead of the regional performance level parameters. For Group 1 and Group 2, we used the same leave-one-out testing: for each subject, the segmentation labels were transferred from the 28 atlases by the same transformation matrices derived in each single LDDMM image mapping and they were fused by STAPLE and Spatial STAPLE. For Group 3, the propagated segmentations from the 29 atlases in Groups 1 and 2 were fused.

To measure the statistical significance of differences between two groups in comparison, instead of using the student's t-test, we applied Fisher's method of randomization. We utilized Monte Carlo simulations to generate 10,000 uniformly distributed random permutations, which gives rise to a collection of t-statistics coming from each permutation. The p-value can then be given by the fraction of times that the t-statistic values from the permutations is larger than the value obtained from the true groups.

3.1 Evaluation of Adding Neighboring Generic Tissue Labels in the Atlases.

In the first experiment, we explored the efficacy of adding neighboring tissue labels around the structures of interest (the sixteen manually delineated subcortical and ventricular structures) in the atlas. The same likelihood-fusion procedure was applied to the two sets of labels of the same atlas images: 1) the sixteen manually defined structures, and 2) the sixteen manually defined structures and the three generic neighboring tissue segmentations—gray matter, white matter, and CSF. A quantitative comparison between the two sets of automated segmentations based on the two different sets of label definitions, in terms of all the three groups, is shown in FIG. 2.

Figure 2:
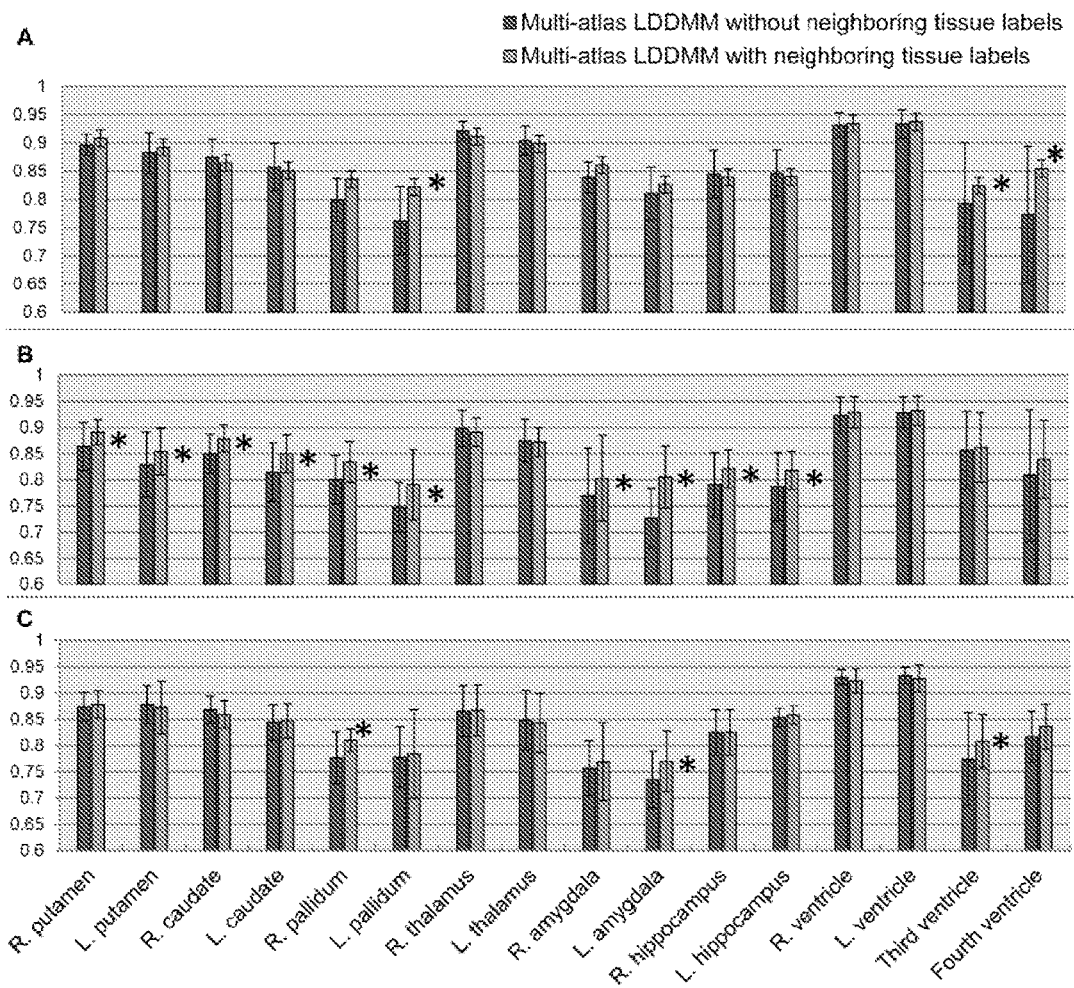
FIG. 2 shows a comparison of two sets of atlas segmentations, according to one embodiment of the invention, according to one embodiment of the invention.

As shown in FIG. 2, adding neighboring tissue labels in the atlases improves the segmentation accuracy for a majority of structures, especially for subjects with dementia (Group 2 & 3). For normal subjects (Group 1), it also helps in the segmentation of certain structures such as pallidum, the $3^{rd}$ ventricle, and the $4^{th}$ ventricle. In addition to the improvements shown via average Dice values, we also observed that adding tissue definitions prevents the mislabeling between ventricles and their neighboring gray matter structure such as hippocampus and amygdala, particularly in the area close to the inferior horn.

Thus in FIG. 2, panels A-C show the mean Dice values and its standard deviations of the sixteen structures, for the three different groups, obtained from likelihood-fusion via multi-atlas LDDMM based on two different sets of atlas label definitions: 1) sixteen manually defined structures (red); 2) sixteen manually defined structures and three generic neighboring tissue segmentations (green).

3.2 Quantitative Evaluation of the Benefit of Multiple Atlases.

Having multiple atlases can increase the computational complexity. We wanted to be able to quantify the advantages of supporting multiple atlas anatomies in the solution. For this we performed multiple experiments. The first compares the performance of segmentation via single-atlas LDDMM using a leave-one-out technique in which a single subject was chosen as a template and all the other subjects in the group were segmented via the LDDMM image mapping procedure. For this purpose, the data in Groups 1 and 2 were combined; one of the 29 subjects was used as the atlas and the other 28 images were segmented. This process was repeated for 29 different atlases implying each subject was segmented 28 times using 28 different atlases. For subjects in Group 3, the single atlases chosen from groups 1 and 2 were used for segmentation to avoid the potential bias of the leave-one-out approach. The mean Dice values and the standard deviations for each set of Dice values for automated segmentations of various structures from single-atlas LDDMM are shown in FIG. 3.

Figure 3:
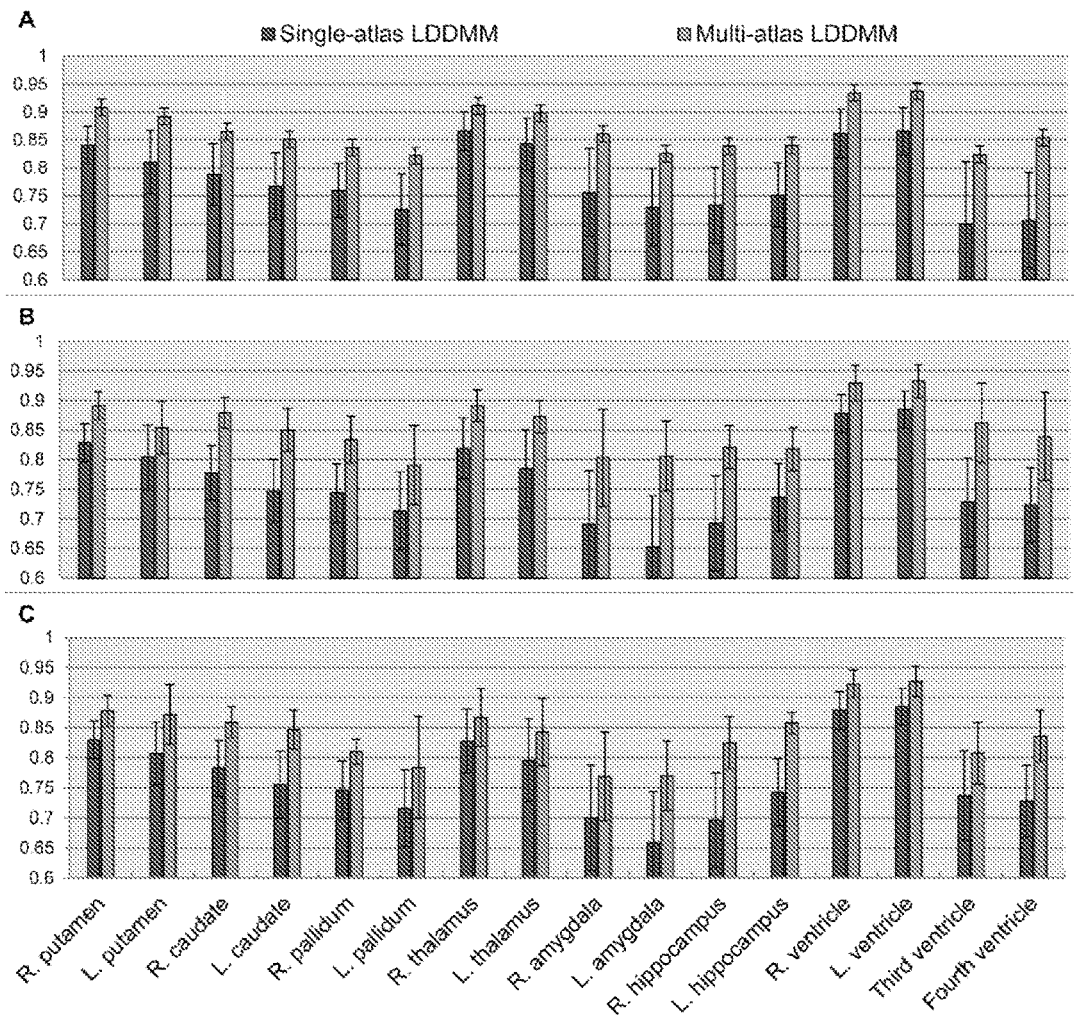
FIG. 3 shows a comparison of segmentation accuracy between single-atlas LDDMM and multi-atlas LDDMM, according to one embodiment of the invention.

As demonstrated in FIG. 3, the single-atlas LDDMM performs relatively poorly in segmenting several of the structures for the Alzheimer's disease (AD) population (Group 2), especially for the amygdala and the hippocampus. These two structures are adjacent to the inferior horn of the ventricles, which tend to have poor segmentation results due to a large topological variability and resultant LDDMM mapping inaccuracy in these areas. Thus in FIG. 3, panels A, B, C respectively show the mean Dice overlaps and the standard deviations of the sixteen structures obtained from single-atlas LDDMM (red) and likelihood-fusion via multi-atlas LDDMM (green) for the three different groups.

Figure 4:
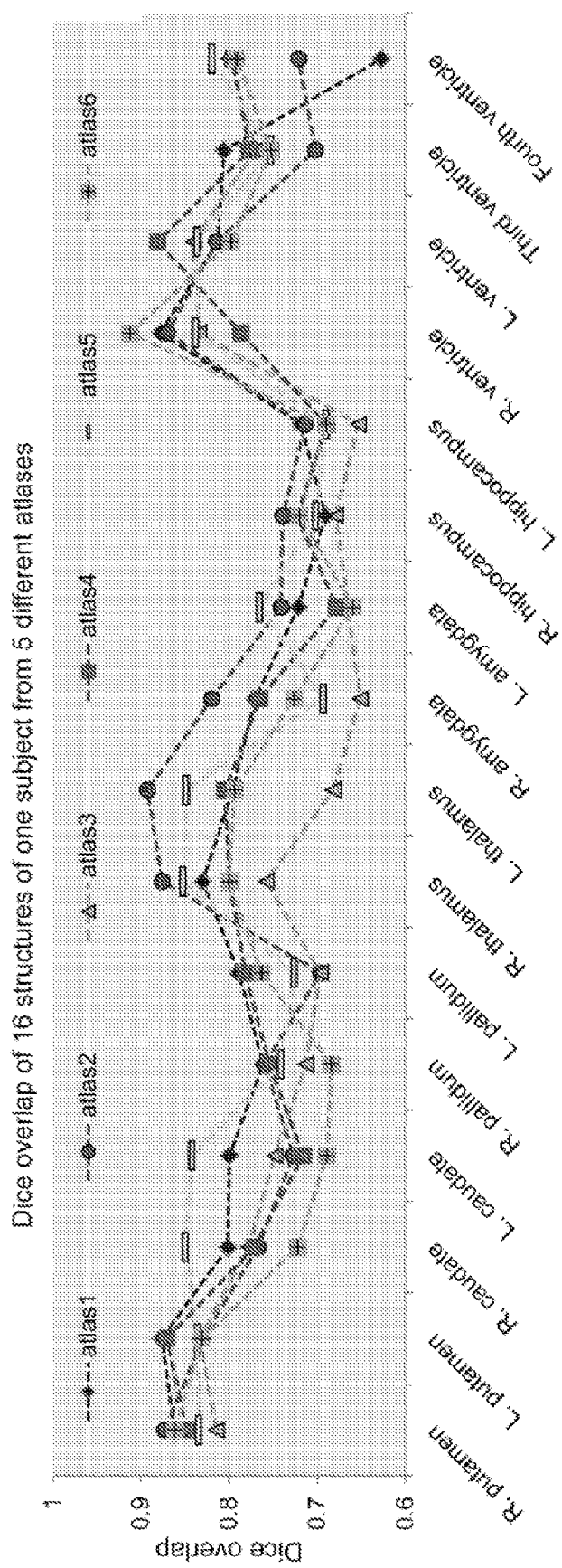
FIG. 4 shows a depiction of the variability within different single atlases, according to one embodiment of the invention.

FIG. 4 shows results for six representative atlases for segmentation of sixteen different structures in one subject. The figure suggests that the best atlas varies depending on the structure; there is no single atlas that outperforms all other over all sixteen structures. For example, for the segmentation of the right putamen and the thalamus in both hemispheres, atlas #2 outperformed other atlases, whereas, for the third ventricle, atlas #2 gave the lowest segmentation accuracy in terms of the Dice overlap. Thus in FIG. 4, Scatterplot of Dice overlaps of automated segmentations of sixteen different structures of one subject from 6 different atlases using single atlas LDDMM.

Figure 5:
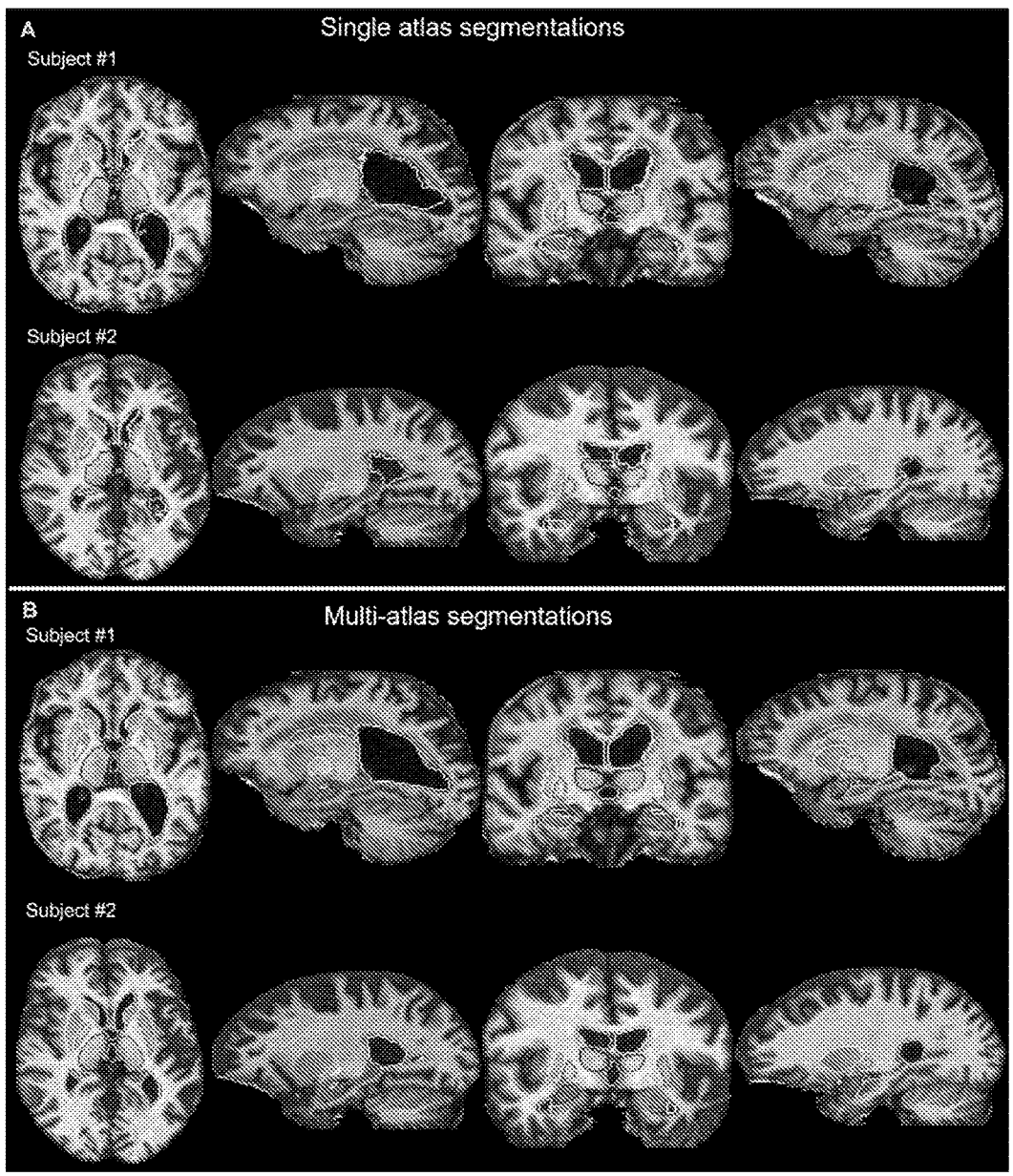
FIG. 5 shows an example of subcortical segmentations from single- and multi-atlas LDDMM approaches, according to one embodiment of the invention.

To contrast to the single-atlas LDDMM case, we examined the likelihood-fusion via multi-atlas LDDMM approach using a series of leave-one-out tests combining the data from Groups 1 and 2. In the leave-one-out strategy, the remaining MRIs form the atlases. FIG. 5 shows the segmentation results of two subjects for a comparison between the single-atlas and the multi-atlas approach. The Dice overlaps that resulted from multi-atlas LDDMM are also demonstrated in FIG. 3 for a direct comparison with that from single-atlas LDDMM. Because of the possibility that the leave-one-out analysis using the data with an identical image protocols (Groups 1 and 2 data) may not represent the real-world performance of the proposed approach, the method was applied to the Group 3 data, which were acquired with a different scanner and imaging parameters. The MRIs from Groups 1 and 2 were taken as the atlases. The Dice overlap for segmentation of Group 3 using the single-atlas and multi-atlas LDDMM is also illustrated in FIG. 3, demonstrating a comparable level of Dice from multi-atlas LDDMM as those obtained in Groups 1 and 2. Thus in FIG. 5, Panel A shows the automated segmentation results of two subjects using single-atlas LDDMM, while panel B shows the segmentation results for the same subjects using multi-atlas LDDMM approach.

Figure 6:
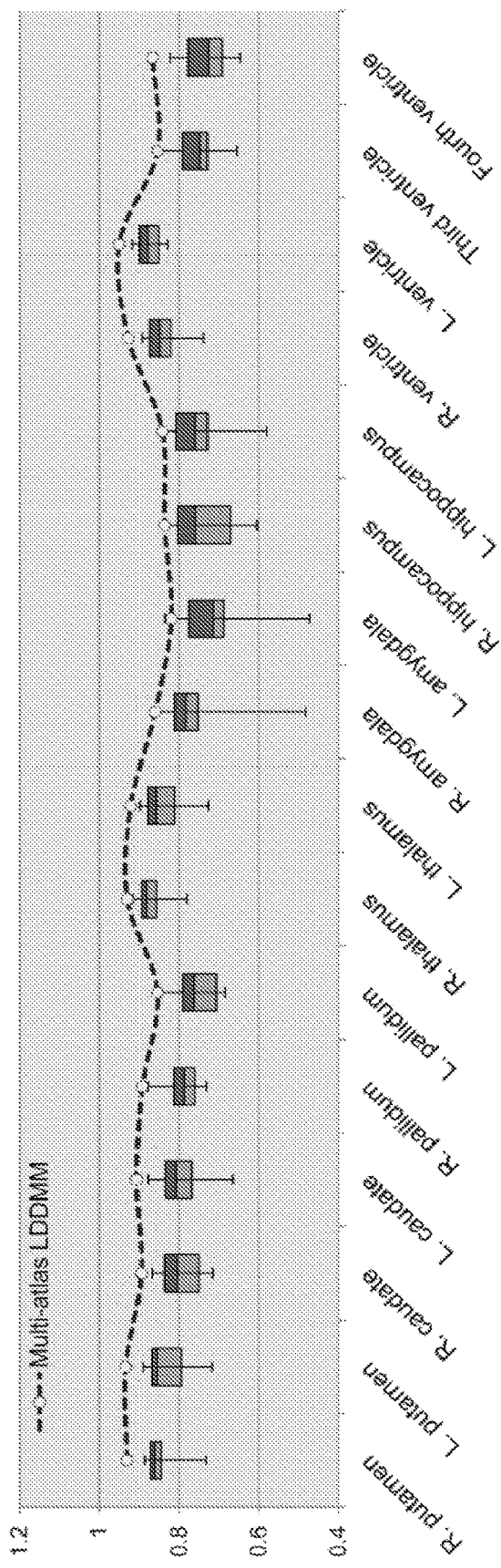
FIG. 6 shows boxplots of the Dice overlaps for sixteen different structures, according to one embodiment of the invention.

FIG. 6 shows the results from one representative case, comparing Dice values of the multi-atlas approach to approaches based on selection of any of the single atlases. This figure clearly shows that likelihood-fusion via multi-atlas LDDMM form an empirical upper bound in performance even for the best combinations of the single-atlas approach for all structures. Regardless of the anatomical variability among these three populations, the multi-atlas approach consistently out-performed the single-atlas approach. For all structures in all three groups, a significant improvement in Dice values has been found with p<0.0005 in the statistical tests. Thus in FIG. 6, the Dice overlaps were computed between the automated segmentations of sixteen different structures of one subject from 28 different atlases using single atlas LDDMM and the one from multi-atlas LDDMM (blue dotted line).

Figure 7:
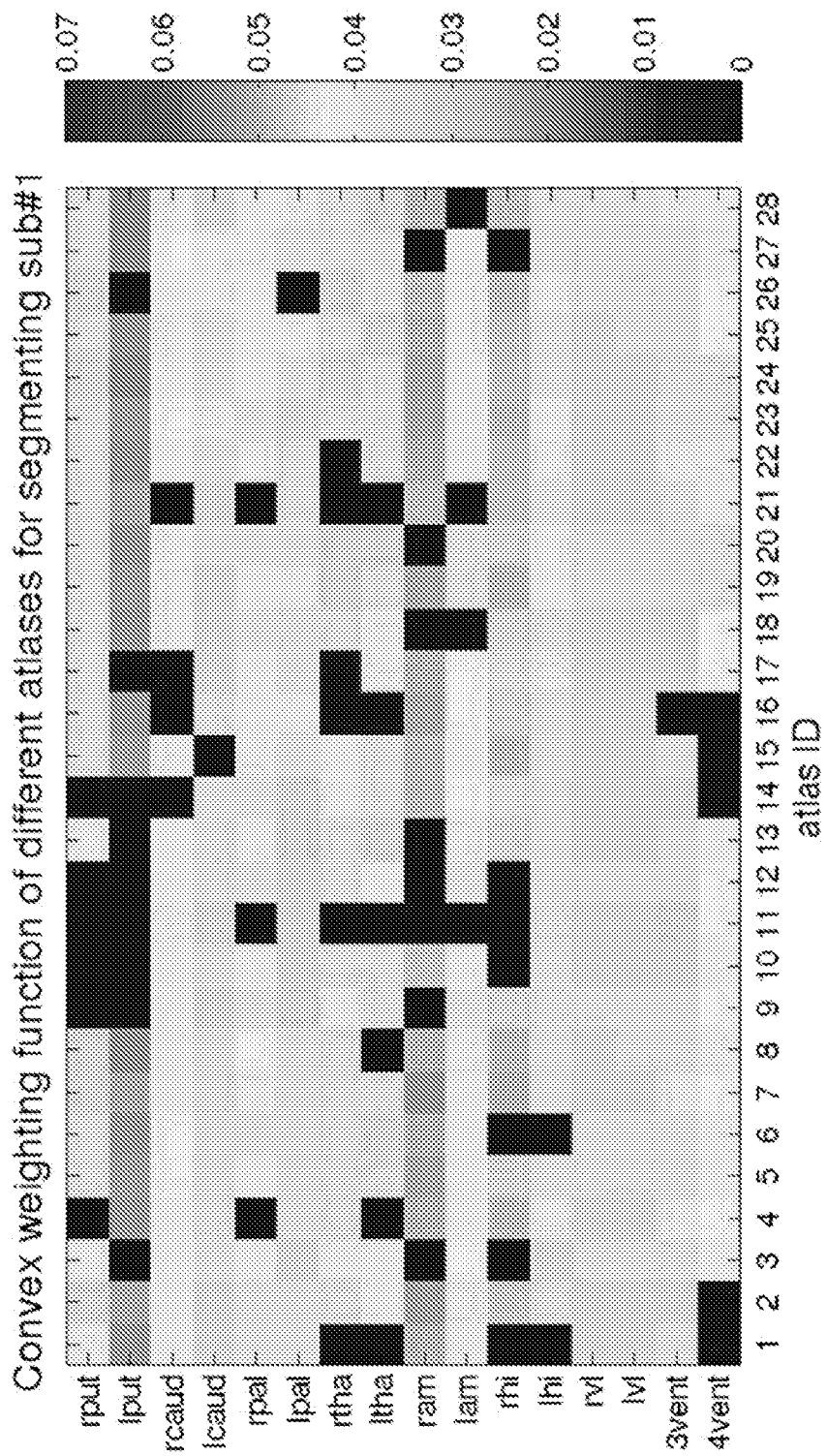
FIG. 7 shows the convex weighting function normalized over each structure, according to one embodiment of the invention.

Shown in FIG. 7 is an examination of the convex weighting function of Eq. (9) for segmenting one subject averaged over voxels i within each single structure j, $$\sum_{i \in struct\#j} \hat{P}_{A_i}(a \mid I, W^{old}) \bigg/ \sum_{i \in struct\#j} 1,$$

a indexed as a function of atlases. As depicted in the figure different atlases contribute different weighting functions when segmenting different structures of the same subject. Thus, in FIG. 7, for each structure, the quantity $$\sum_{i \in struct\#j} \hat{P}_{A_i}(a \mid I, W^{old}) \bigg/ \sum_{i \in struct\#j} 1$$

that is depicted for each atlas (column) and each of the 16 structures (rows), is color-coded.

Figure 8:
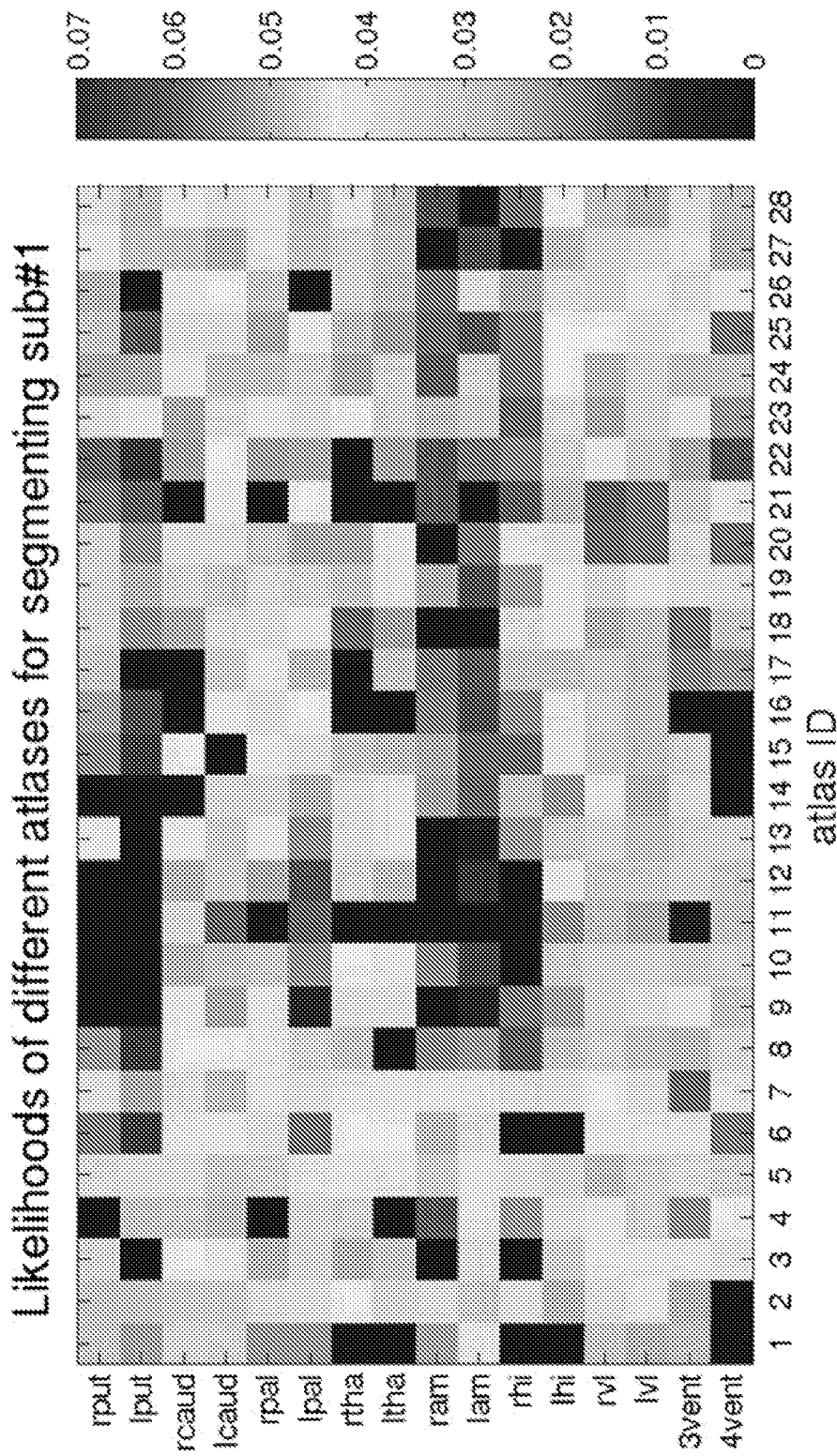
FIG. 8 shows the likelihood contribution of each atlas averaged over the atlas structures, according to one embodiment of the invention.

Shown in FIG. 8 is a depiction of the likelihood contribution of each atlas in the likelihood fusion equation $$\sum_{i \in struct\#j} \hat{P}_{A_i}(a \mid I, W^{old}) \max_\varphi p(I_i, W_i^{old}, \varphi \mid a) \bigg/ \sum_{i \in struct\#j} 1$$

averaged over each of the 16 structures (rows) depicted for each of the twenty-eight atlases (columns). Thus, in FIG. 8, the quantity $$\sum_{i \in struct\#j} \hat{P}_{A_i}(a \mid I, W^{old}) \max_\varphi p(I_i, W_i^{old}, \varphi \mid a) \bigg/ \sum_{i \in struct\#j} 1$$

can be obtained from the 28 different atlases (columns) for each structure (row).

Figure 9:
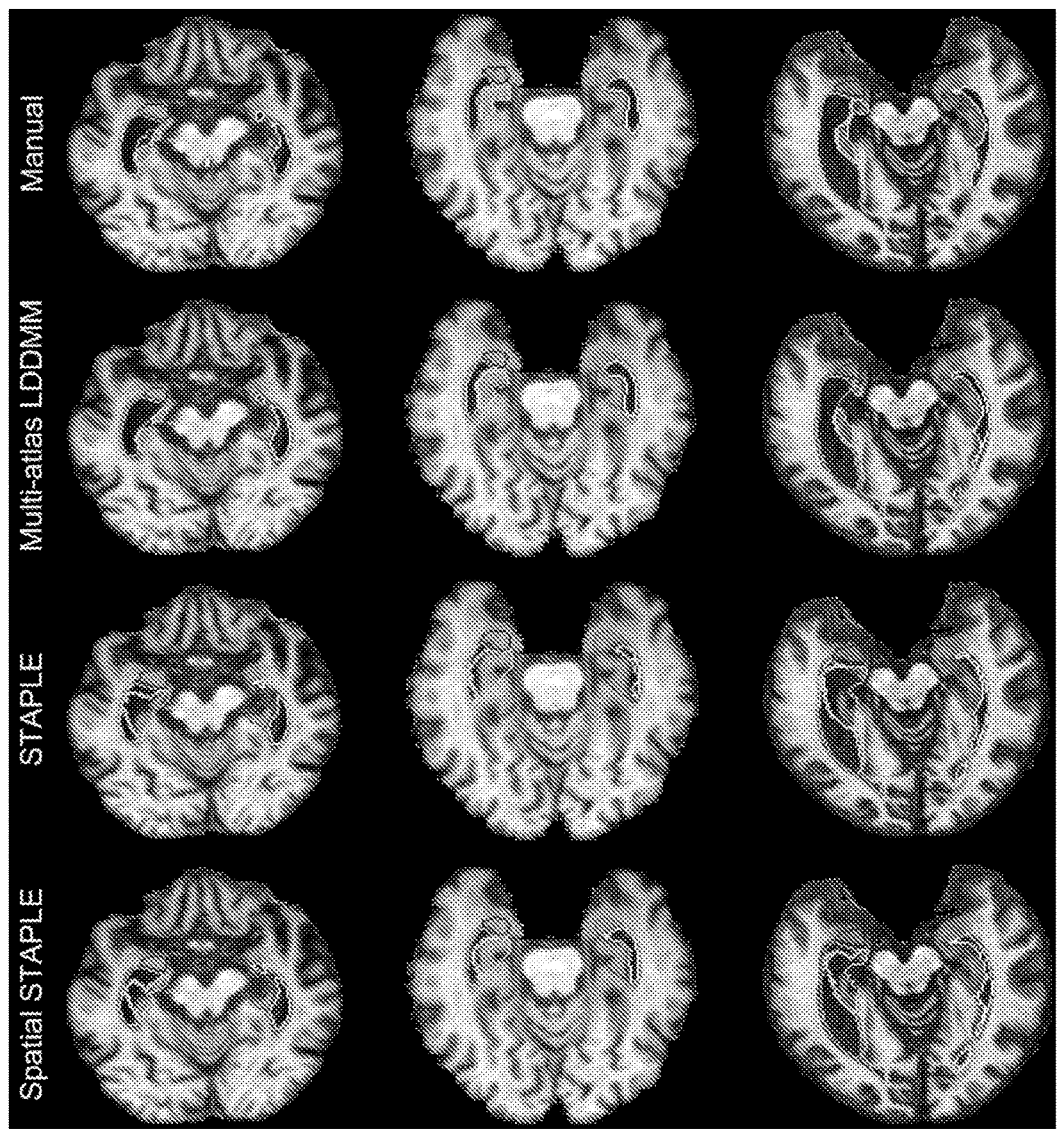
FIG. 9 shows example slices for a comparison of multi-atlas LDDMM, STAPLE, and Spatial STAPLE, according to one embodiment of the invention.

FIG. 9 shows three representative 2-D slices of three structures near medial temporal regions—the amygdala, the hippocampus, and the ventricle in both hemispheres obtained respectively from manual delineation (top row), likelihood-fusion via multi-atlas LDDMM (2nd row), STAPLE (3rd row), and Spatial STAPLE (bottom row).

3.3 Comparisons to Segmentation Averaging (STAPLE & Spatial STAPLE)

The generative probability model, which multi-atlas LDDMM is based, averages likelihoods generating a single label for each segmentation voxel. It is natural to compare to competitive methods which average segmentation labels via label fusion. For this we compared the multi-atlas LDDMM with two representative label fusion techniques, STAPLE [46] and Spatial STAPLE [58]. One might expect that while label fusion should be more robust to images for which the generative model is not accurate, likelihood fusion should provide benefits in circumstances when the generative model is valid. Tables 2-4 tabulate the mean values and standard deviations of the Dice overlaps for the three methods computed across subjects in the three groups. The performance of Spatial STAPLE and likelihood-fusion via multi-atlas LDDMM were almost identical for the control group (Table 2), providing superior performance relative to STAPLE. For the brains from patient populations, significant improvement by likelihood-fusion via multi-atlas LDDMM over Spatial STAPLE was observed for 9 structures in the AD (Table 3) and 3 structures in the primary progressive aphasia (PPA) populations (Table 4). A notable improvement was found in the area around the inferior and posterior horns of the lateral ventricles, where the ventricle anatomy has a substantial amount of anatomical variability (FIG. 9). The benefit must be arising from the fact even though these anatomies are disease we are able to do an adequate job of modeling the generative probability therefore the atlas selector function is effectively averaging in the proper likelihoods which fit the anatomies.

Discussion

As accurate segmentation is at the center of many neuropsychiatric studies, there have been many methods developed for brain segmentation, which are typically based on local approaches mostly involving multi-compartment appearance and Gaussian mixture modeling, coupled to MAP or maximum-likelihood [53,59-69]. To introduce constraints between voxels, Markov random fields and level sets are two examples of locally-defined prior distributions enforcing interactions at the voxel level [1,70-78]. Similar appearance modeling is used in the deformable template approaches as the matching cost functions; the higher level relationships are inherited from the templates. The MAP segmentation we used is a direct generalization of the MAP approach originally articulated by [1] in which global constraints are introduced via Markov random field conditional probability structure at the segmentation layer. The approach here is based on the diffeomorphic orbit model to induce neighborhood dependence at the random field level.

The conditionally Gaussian random field model used throughout is the generative random orbit model used for "template" estimation [39,79,80]. Whereas, for template estimation, the template and the diffeomorphism of the hyper-template are the unknown, and the population contributes through the conditional likelihood functions associated to each of the multiple anatomical coordinate systems in the atlas set. In this paper, the segmentation field plays the role of the unknown, and the population is represented via the charts in the atlases.

In these global deformable template methods, templates which are far in the deformation space are less accurate for representing anatomical features and parameters being estimated. In the context of segmentation, multiple atlas based methods which embed the global solution with more locally accurate properties via label combination have been used extensively [37,46]. The multi-label interpretation approach, as described in [46], enters into our method only indirectly, as we interpret each voxel position in the anatomical target subject as arising from any of the given atlases. Therefore, this can be interpreted by the Bayesian conditional probability of each atlas chart contribution conditioned on the image. The method described here fuses the atlases via convex combination of the atlas-specific likelihoods, with the weights in the convex combination given by the conditional-mean formula, and never explicitly generates the atlas-specific segmentations of the target MRI. The purpose of the conditional-mean framework of the EM algorithm is to remove the explicit dependence of the estimation of the target segmentation on the high dimensional nature of the nuisance variables. It serves the same purpose as in [39] and [80]—the nuisance fields do not grow with the number of atlases, which could have the disadvantage that it would make segmentation of the target MRI inconsistent.

Another aspect of the diffeomorphic framework is that since we can model human anatomy via the diffeomorphism metric as a complete metric space [35,55,81,82], our weighting in the MAP solution is specified via the metric distance between atlases and the subject. Similar to the method proposed in [48], this allows us to introduce a robust decision procedure, which decreases the computational complexity by removing atlases that are large in metric distance.

The proposed method has been tested based on three datasets with different pathologies—normal aging, subjects with Alzheimer's disease, and subjects with dementia. Likelihood-fusion via multi-atlas LDDMM improves the segmentation accuracy obtained from single-atlas LDDMM. Favorable comparison to label-fusion methods is also evident as shown in Tables 2-4.

Compared with other recently published segmentation methods and the reported Dice overlaps, our method demonstrates comparable or favorable levels of segmentation accuracy, with mean Dice overlap results in the range of 0.8 to 0.93. A direct comparison of segmentation accuracy among different programs is difficult as many programs contain internal structural definition with the resultant differences in performance which can simply reflect the way that structures are defined. Given the structure sizes and the intensity ranges, it is generally considered more difficult to automatically segment the hippocampus and amygdala than other deep gray matter structures. Previous publications such as [83] have reported Dice values such as 0.73 and 0.76 for the hippocampus, and [84] has reported Dice overlaps on the order of 0.75 for the amygdala using either FreeSurfer [1] and FSL [69]. In a recent work specifically on the segmentation of hippocampus, [85] reported Dice of 0.88 for the best performing subjects while 0.78 for the worst subjects. [86] reported hippocampus segmentations with mean Dice 0.83. Our results compare favorably, although it is difficult to directly compare Dice values from different studies given the difference that may be caused by the dataset used, the image acquisition protocol, or the quality and the protocol of manual segmentations. One future direction should be evaluating the proposed method on some more widely studies datasets so as to be comparable with other existing segmentation methods [86,87]. We have chosen to focus our study on populations with severe atrophy and the reported Dice values should represent more realistic performance than those based only on young healthy subjects such as those reported in [85]. As shown in FIG. 5, in addition to the accuracy reports, the likelihood-fusion approach in the diffeomorphic setting exhibits smooth boundaries for the segmentations, which is not typical in the usual intensity-based segmentation approaches.

The current work has focused on subcortical and ventricular regions. Our initial investigation into whole brain segmentation setting via likelihood-fusion has been validated in a limited setting in [88]. We might expect that the very simple model of conditionally Gaussian (essentially single compartment modeling of the intensity) can be significantly improved via the incorporation of multi-compartment mixture modeling such as in [53]. In addition, the results presented in this paper only make use of T1-weighted images. Incorporating multi-modality data (T2, diffusion) information into our approach should increase the segmentation accuracy. A clear potential limitation of this method is that it requires manual labeling of multiple atlases, which is more labor-intensive compared to the single-atlas approach, and increases the computational complexity by O(N), where N denotes the number of atlases.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

TABLE 1

Three different groups of MR scans and their respective size, age range, resolution, imaging protocol, and pathology. NC indicates normal controls, AD indicates Alzheimer's disease. PPA indicates primary progressive aphasia

| Group | Size | Age range | Resolution (mm) | Imaging protocol | Patient group |
|---|---|---|---|---|---|
| 1 | 14 | 55 to 85 | 0.9375 × 0.9375 × 1.2 | 3.0T | NC elder |
| 2 | 15 | 56 to 87 | 0.9375 × 0.9375 × 1.2 | 3.0T | AD |
| 3 | 6 | 51 to 84 | 0.8984 × 0.8984 × 1.0 | 3.0T | Dementia (PPA) |

TABLE 2

The average Dice overlaps between manual volume and the automated volume measured over the fourteen datasets of the first group for each structure for comparisons of STAPLE, Spatial STAPLE, and likelihood-fusion via multi-atlas LDDMM. Bold typesetting indicates that the Dice overlap ratio obtained from the corresponding is statistically significant higher than that of other methods ($p < 0.05$).

| | STAPLE | Spatial STAPLE | multi-atlas LDDMM |
|---|---|---|---|
| R. putamen | 0.878 (0.0250) | 0.908 (0.0154) | 0.908 (0.0148) |
| L. putamen | 0.857 (0.0362) | 0.891 (0.0350) | 0.892 (0.0329) |
| R. caudate | 0.836 (0.0409) | 0.867 (0.0355) | 0.865 (0.0446) |
| L. caudate | 0.812 (0.0506) | 0.852 (0.0365) | 0.851 (0.0465) |
| R. pallidum | 0.776 (0.0357) | 0.840 (0.0291) | 0.836 (0.0378) |
| L. pallidum | 0.730 (0.0543) | 0.817 (0.0501) | 0.822 (0.0463) |
| R. thalamus | 0.907 (0.0224) | 0.911 (0.0183) | 0.911 (0.0185) |
| L. thalamus | 0.883 (0.0370) | 0.906 (0.0246) | 0.898 (0.0199) |
| R. amygdala | 0.786 (0.0401) | 0.862 (0.0245) | 0.861 (0.0188) |
| L. amygdala | 0.767 (0.0527) | 0.822 (0.0393) | 0.826 (0.0388) |
| R. hippocampus | 0.769 (0.0461) | 0.838 (0.0337) | 0.839 (0.0297) |
| L. hippocampus | 0.795 (0.0499) | 0.846 (0.0278) | 0.840 (0.0227) |
| R. ventricle | 0.874 (0.0465) | 0.917 (0.0267) | 0.934 (0.0247) |
| L. ventricle | 0.880 (0.0503) | 0.918 (0.0336) | 0.937 (0.0259) |
| Third ventricle | 0.548 (0.1712) | 0.776 (0.1214) | 0.824 (0.0817) |
| Fourth ventricle | 0.671 (0.1287) | 0.799 (0.0931) | 0.854 (0.0776) |

TABLE 3

Mean and standard deviations of Dice overlaps computed across the fifteen subjects in the second group for each structure for comparisons of STAPLE, Spatial STAPLE, and likelihood-fusion via multi-atlas LDDMM. Bold typesetting indicates that the Dice overlap ratio obtained from the corresponding is statistically significant higher than that of other methods ($p < 0.05$).

|  | STAPLE | Spatial STAPLE | multi-atlas LDDMM |
|---|---|---|---|
| R. putamen | 0.838 (0.0504) | 0.878 (0.0351) | 0.891 (0.0238) |
| L. putamen | 0.813 (0.0661) | 0.848 (0.0525) | 0.854 (0.0444) |
| R. caudate | 0.776 (0.0558) | 0.856 (0.0346) | 0.879 (0.0260) |
| L. caudate | 0.746 (0.0696) | 0.828 (0.0454) | 0.850 (0.0359) |
| R. pallidum | 0.784 (0.0547) | 0.831 (0.0389) | 0.834 (0.0392) |
| L. pallidum | 0.746 (0.0475) | 0.792 (0.0522) | 0.791 (0.0668) |
| R. thalamus | 0.881 (0.0355) | 0.900 (0.0313) | 0.891 (0.0270) |
| L. thalamus | 0.855 (0.0541) | 0.876 (0.0381) | 0.872 (0.0275) |
| R. amygdala | 0.703 (0.0974) | 0.796 (0.0948) | 0.803 (0.0816) |
| L. amygdala | 0.647 (0.0708) | 0.785 (0.0647) | 0.806 (0.0592) |
| R. hippocampus | 0.670 (0.0988) | 0.783 (0.0759) | 0.821 (0.0362) |
| L. hippocampus | 0.703 (0.0859) | 0.799 (0.0556) | 0.818 (0.0363) |
| R. ventricle | 0.904 (0.0481) | 0.917 (0.0326) | 0.929 (0.0299) |
| L. ventricle | 0.908 (0.0466) | 0.921 (0.0333) | 0.932 (0.0278) |
| Third ventricle | 0.678 (0.1244) | 0.830 (0.0426) | 0.862 (0.0668) |
| Fourth ventricle | 0.706 (0.1245) | 0.793 (0.0862) | 0.839 (0.0741) |

TABLE 4

Mean and standard deviations of Dice overlaps obtained respectively from STAPLE, Spatial STAPLE, and likelihood-fusion via multi-atlas LDDMM in segmenting the 16 structures of the six subjects in the third group. Bold typesetting indicates that the Dice overlap ratio obtained from the corresponding is statistically significant higher than that of other methods ($p < 0.05$).

|  | STAPLE | Spatial STAPLE | multi-atlas LDDMM |
|---|---|---|---|
| R. putamen | 0.866 (0.0297) | 0.884 (0.0166) | 0.878 (0.0260) |
| L. putamen | 0.856 (0.0392) | 0.878 (0.0413) | 0.872 (0.0499) |
| R. caudate | 0.861 (0.0327) | 0.854 (0.0253) | 0.859 (0.0258) |
| L. caudate | 0.832 (0.0432) | 0.836 (0.0218) | 0.847 (0.0322) |
| R. pallidum | 0.788 (0.0393) | 0.817 (0.0261) | 0.810 (0.0212) |
| L. pallidum | 0.763 (0.0520) | 0.777 (0.0686) | 0.784 (0.0847) |
| R. thalamus | 0.871 (0.0298) | 0.854 (0.0494) | 0.867 (0.0482) |
| L. thalamus | 0.849 (0.0415) | 0.828 (0.0546) | 0.843 (0.0563) |
| R. amygdala | 0.707 (0.0568) | 0.769 (0.0668) | 0.769 (0.0741) |
| L. amygdala | 0.662 (0.0752) | 0.745 (0.0561) | 0.770 (0.0580) |
| R. hippocampus | 0.777 (0.0987) | 0.796 (0.0385) | 0.825 (0.0432) |
| L. hippocampus | 0.805 (0.0251) | 0.839 (0.0236) | 0.858 (0.0174) |
| R. ventricle | 0.927 (0.0144) | 0.924 (0.0192) | 0.923 (0.0229) |
| L. ventricle | 0.927 (0.0246) | 0.926 (0.0201) | 0.927 (0.0255) |
| Third ventricle | 0.749 (0.1034) | 0.803 (0.0327) | 0.808 (0.0511) |
| Fourth ventricle | 0.738 (0.0487) | 0.811 (0.0292) | 0.836 (0.0428) |

REFERENCES

1. Fischl B, Salat D H, Busa E, Albert M, Dieterich M, et al. (2002) Whole brain segmentation: Automated labeling of neuroanatomical structures in the human brain. Neuron 33: 341-355.
2. Rex D E, Ma J Q, Toga A W (2003) The LONI pipeline processing environment. Neuroimage 19: 1033-1048.
3. Jiang H, van Zijl P C, Kim J, Pearlson G D, Mori S (2006) DtiStudio: Resource program for diffusion tensor computation and fiber bundle tracking. Comput Methods Programs Biomed 81: 106-116.
4. Friston K J, Ashburner J, Kiebel S J, Nichols T E, Penny W D, editors. (2007) Statistical parametric mapping: The analysis of functional brain images: Academic Press.
5. Woolrich M W, Jbabdi S, Patenaude B, Chappell M, Makni S, et al. (2009) Bayesian analysis of neuroimaging data in FSL. Neuroimage 45: S173-86.
6. Talairach J, Tournoux P (1988) Co-planar stereotaxic atlas of the human brain: Thieme N.Y.
7. Evans A C, Marrett S, Neelin P, Collins L, Worsley K, et al. (1992) Anatomical mapping of functional activation in stereotactic coordinate space. Neuroimage 1: 43-53.
8. Mazziotta J C, Toga A W, Evans A, Fox P, Lancaster J (1995) A probabilistic atlas of the human brain: Theory and rationale for its development. the international consortium for brain mapping (ICBM). Neuroimage 2: 89-101.
9. Holmes C J, Hoge R, Collins L, Woods R, Toga A W, et al. (1998) Enhancement of MR images using registration for signal averaging. J Comput Assist Tomogr 22: 324-333.
10. Mazziotta J, Toga A, Evans A, Fox P, Lancaster J, et al. (2001) A probabilistic atlas and reference system for the human brain: International consortium for brain mapping (ICBM). Philosophical Transactions of the Royal Society of London Series B: Biological Sciences 356: 1293-1322.
11. Fonov V, Evans A C, Botteron K, Almli C R, McKinstry R C, et al. (2011) Unbiased average age-appropriate atlases for pediatric studies. Neuroimage 54: 313-327.
12. Wakana S, Jiang H, Nagae-Poetscher L M, van Zijl P C, Mori S (2004) Fiber tract-based atlas of human white matter anatomy. Radiology 230: 77-87.
13. Mori S, Wakana S, van Zijl P C M, Nagae-Poetscher L M (2005) MRI atlas of human white matter: Elsevier Science.
14. Catani M, Thiebaut de Schotten M (2008) A diffusion tensor imaging tractography atlas for virtual in vivo dissections. Cortex 44: 1105-1132.
15. Mori S, Oishi K, Jiang H, Jiang L, Li X, et al. (2008) Stereotaxic white matter atlas based on diffusion tensor imaging in an ICBM template. Neuroimage 40: 570-582.
16. Oishi K, Zilles K, Amunts K, Faria A, Jiang H, et al. (2008) Human brain white matter atlas: Identification and assignment of common anatomical structures in superficial white matter. Neuroimage 43: 447-457.
17. Verhoeven J S, Sage C A, Leemans A, Van Hecke W, Callaert D, et al. (2010) Construction of a stereotaxic DTI atlas with full diffusion tensor information for studying white matter maturation from childhood to adolescence using tractography-based segmentations. Hum Brain Mapp 31: 470-486.
18. Drury H A, Van Essen D C, Anderson C H, Lee C W, Coogan T A, et al. (1996) Computerized mappings of the cerebral cortex. A multiresolution flattening method and a surface-based coordinate system. J Cogn Neurosci 8: 1-28.
19. Dale A M, Fischl B, Sereno M I (1999) Cortical surface-based analysis. I. segmentation and surface reconstruction. Neuroimage 9: 179-194.
20. Fischl B, Sereno M I, Tootell R B H, Dale A M (1999) High-resolution intersubject averaging and a coordinate system for the cortical surface. Hum Brain Mapp 8: 272-284.
21. Van Essen D C (2005) A population-average, landmark- and surface-based (PALS) atlas of human cerebral cortex. Neuroimage 28: 635-662.
22. Evans A C, Janke A L, Collins D L, Baillet S (2012) Brain templates and atlases. Neuroimage 62: 911-922.

23. Bajcsy R, Lieberson R, Reivich M (1983) A computerized system for the elastic matching of deformed radiographic images to idealized atlas images. J Comput Assist Tomogr 7: 618-625.
24. Bajcsy R, Kovačič S (1989) Multiresolution elastic matching. Computer Vision, Graphics, and Image Processing 46: 1-21.
25. Miller M I, Christensen G E, Amit Y, Grenander U (1993) Mathematical textbook of deformable neuroanatomies. Proc Natl Acad Sci USA 90: 11944-11948.
26. Collins D L, Holmes C J, Peters T M, Evans A C (1995) Automatic 3-D model-based neuroanatomical segmentation. Hum Brain Mapp 3: 190-208.
27. Christensen G E, Joshi S C, Miller M I (1997) Volumetric transformation of brain anatomy. IEEE Trans Med Imaging 16: 864-877.
28. Collins D, Evans A (1997) Animal: Validation and applications of nonlinear registration-based segmentation. Intern. J. Pattern Recognit. Artif. Intell. 11: 1271-1294.
29. Haller J W, Banerjee A, Christensen G E, Gado M, Joshi S, et al. (1997) Three-dimensional hippocampal MR morphometry with high-dimensional transformation of a neuroanatomic atlas. Radiology 202: 504-510.
30. Dupuis P, Grenander U, Miller M I (1998) Variational problems on flows of diffeomorphisms for image matching. Quart. Appl. Math. 56: 587-600.
31. Grenander U, Miller M I (1998) Computational anatomy: An emerging discipline. Q Appl Math LVI: 617-694.
32. Warfield S, Robatino A, Dengler J, Jolesz F, Kikinis R (1999) Nonlinear registration and template driven segmentation. Brain Warping 4: 67-84.
33. Hogan R E, Mark K E, Wang L, Joshi S, Miller M I, et al. (2000) Mesial temporal sclerosis and temporal lobe epilepsy: MR imaging deformation-based segmentation of the hippocampus in five patients. Radiology 216: 291-297.
34. Crum W R, Scahill R I, Fox N C (2001) Automated hippocampal segmentation by regional fluid registration of serial MRI: Validation and application in alzheimer's disease. Neuroimage 13: 847-855.
35. Miller M I, Trouve A, Younes L (2002) On the metrics and euler-lagrange equations of computational anatomy. Annu Rev Biomed Eng 4: 375-405.
36. Carmichael O T, Aizenstein H A, Davis S W, Becker J T, Thompson P M, et al. (2005) Atlas-based hippocampus segmentation in alzheimer's disease and mild cognitive impairment. Neuroimage 27: 979-990.
37. Heckemann R A, Hajnal J V, Aljabar P, Rueckert D, Hammers A (2006) Automatic anatomical brain MRI segmentation combining label propagation and decision fusion. Neuroimage 33: 115-126.
38. Pohl K M, Fisher J, Grimson W E L, Kikinis R, Wells W M (2006) A bayesian model for joint segmentation and registration. Neuroimage 31: 228-239.
39. Ma J, Miller M I, Trouve A, Younes L (2008) Bayesian template estimation in computational anatomy. Neuroimage 42: 252-261.
40. Grenander U (1993) General pattern theory: Oxford University Press.
41. Dempster A P, Laird N M, Rubin D B (1977) Maximum likelihood from incomplete data via the EM algorithm. Journal of the Royal Statistical Society. Series B (Methodological) 39: pp. 1-38.
42. Boothby W M (1986) An introduction to differentiable manifolds and riemannian geometry: Academic Press.
43. Kittler J, Hatef M, Duin R P W, Matas J (1998) On combining classifiers. Pattern Analysis and Machine Intelligence, IEEE Transactions on 20: 226-239.
44. Kittler J, Alkoot F M (2003) Sum versus vote fusion in multiple classifier systems. Pattern Analysis and Machine Intelligence, IEEE Transactions on 25: 110-115.
45. Rohlfing T, Brandt R, Menzel R, Maurer C R, Jr. (2004) Evaluation of atlas selection strategies for atlas-based image segmentation with application to confocal microscopy images of bee brains. Neuroimage 21: 1428-1442.
46. Warfield S K, Zou K H, Wells W M (2004) Simultaneous truth and performance level estimation (STAPLE): An algorithm for the validation of image segmentation. IEEE Trans Med Imaging 23: 903-921.
47. Artaechevarria X, Munoz-Barrutia A, Ortiz-de-Solorzano C (2009) Combination strategies in multi-atlas image segmentation: Application to brain MR data. Medical Imaging, IEEE Transactions on 28: 1266-1277.
48. Langerak T R, van der Heide U A, Kotte A N T J, Viergever M A, van Vulpen M, et al. (2010) Label fusion in atlas-based segmentation using a selective and iterative method for performance level estimation (SIMPLE). Medical Imaging, IEEE Transactions on 29: 2000-2008.
49. Lotjonen J M, Wolz R, Koikkalainen J R, Thurfjell L, Waldemar G, et al. (2010) Fast and robust multi-atlas segmentation of brain magnetic resonance images. Neuroimage 49: 2352-2365.
50. Aljabar P, Heckemann R A, Hammers A, Hajnal J V, Rueckert D (2009) Multi-atlas based segmentation of brain images: Atlas selection and its effect on accuracy. Neuroimage 46: 726-738.
51. van Rikxoort E M, Isgum I, Arzhaeva Y, Staring M, Klein S, et al. (2010) Adaptive local multi-atlas segmentation: Application to the heart and the caudate nucleus. Med Image Anal 14: 39-49.
52. Sabuncu M R, Yeo B T T, Van Leemput K, Fischl B, Golland P (2010) A generative model for image segmentation based on label fusion. Medical Imaging, IEEE Transactions on 29: 1714-1729.
53. Priebe C E, Miller M I, Ratnanather J T (2006) Segmenting magnetic resonance images via hierarchical mixture modelling. Comput Stat Data Anal 50: 551-567.
54. Beg M F, Miller M I, Trouvé A, Younes L (2005) Computing large deformation metric mappings via geodesic flows of diffeomorphisms. International Journal of Computer Vision 61: 139-157.
55. Miller M I, Trouve A, Younes L (2006) Geodesic shooting for computational anatomy. J Math Imaging Vis 24: 209-228.
56. Ceritoglu C, Oishi K, Li X, Chou M C, Younes L, et al. (2009) Multi-contrast large deformation diffeomorphic metric mapping for diffusion tensor imaging. Neuroimage 47: 618-627.
57. Vaillant M, Glaunès J (2005) Surface matching via currents. 3565: 1-5.
58. Asman A J, Landman B A (2012) Formulating spatially varying performance in the statistical fusion framework. Medical Imaging, IEEE Transactions on 31: 1326-1336.
59. Cootes T F, Hill A, Taylor C J, Haslam J (1994) Use of active shape models for locating structures in medical images.—Image and Vision Computing 12: 355-365.
60. Wells III W, Grimson W E L, Kikinis R, Jolesz F A (1996) Adaptive segmentation of MRI data. Medical Imaging, IEEE Transactions on 15: 429-442.
61. Duta N, Sonka M (1998) Segmentation and interpretation of MR brain images: An improved active shape model. IEEE Trans Med Imaging 17: 1049-1062.

62. Pham D L, Prince J L (1999) Adaptive fuzzy segmentation of magnetic resonance images. IEEE Trans Med Imaging 18: 737-752.
63. Mitchell S C, Lelieveldt B P, van der Geest R J, Bosch H G, Reiber J H, et al. (2001) Multistage hybrid active appearance model matching: Segmentation of left and right ventricles in cardiac MR images. IEEE Trans Med Imaging 20: 415-423.
64. Shen D, Herskovits E H, Davatzikos C (2001) An adaptive-focus statistical shape model for segmentation and shape modeling of 3-D brain structures. IEEE Trans Med Imaging 20: 257-270.
65. van Ginneken B, Frangi A F, Staal J J, ter Haar Romeny B M, Viergever M A (2002) Active shape model segmentation with optimal features. IEEE Trans Med Imaging 21: 924-933.
66. Van Leemput K, Maes F, Vandermeulen D, Suetens P (2003) A unifying framework for partial volume segmentation of brain MR images. Medical Imaging, IEEE Transactions on 22: 105-119.
67. Awate S P, Gee J C (2007) A fuzzy, nonparametric segmentation framework for DTI and MRI analysis. Inf Process Med Imaging 20: 296-307.
68. Tu Z, Narr K L, Dollar P, Dinov I, Thompson P M, et al. (2008) Brain anatomical structure segmentation by hybrid discriminative/generative models. IEEE Trans Med Imaging 27: 495-508.
69. Patenaude B, Smith S M, Kennedy D N, Jenkinson M (2011) A bayesian model of shape and appearance for subcortical brain segmentation. Neuroimage 56: 907-922.
70. Dubes R C, Jain A K, Nadabar S G, Chen C C (1990) MRF model-based algorithms for image segmentation. Pattern Recognition, 1990 Proceedings, 10th International Conference on i: 808-814 vol. 1.
71. Held K, Rota Kops E, Krause B J, Wells W M, 3rd, Kikinis R, et al. (1997) Markov random field segmentation of brain MR images. IEEE Trans Med Imaging 16: 878-886.
72. Baillard C, Barillot C (2000) Robust 3D segmentation of anatomical structures with Level Sets. 1935: 236-245.
73. Baillard C, Hellier P, Barillot C (2001) Segmentation of brain 3D MR images using level sets and dense registration. Med Image Anal 5: 185-194.
74. Zhang Y, Brady M, Smith S (2001) Segmentation of brain MR images through a hidden markov random field model and the expectation-maximization algorithm. Medical Imaging, IEEE Transactions on 20: 45-57.
75. Vese L A, Chan T F (2002) A multiphase level set framework for image segmentation using the mumford and shah model. International Journal of Computer Vision 50: 271-293.
76. Han X, Xu C, Prince J L (2003) A topology preserving level set method for geometric deformable models. Pattern Analysis and Machine Intelligence, IEEE Transactions on 25: 755-768.
77. Paragios N (2003) A level set approach for shape-driven segmentation and tracking of the left ventricle. Medical Imaging, IEEE Transactions on 22: 773-776.
78. Yang J, Duncan J S (2004) 3D image segmentation of deformable objects with joint shape-intensity prior models using level sets. Med Image Anal 8: 285-294.
79. Allassonnière S, Amit Y, Trouvé A (2007) Towards a coherent statistical framework for dense deformable template estimation. Journal of the Royal Statistical Society: Series B (Statistical Methodology) 69: 3-29.
80. Ma J, Miller M I, Younes L (2010) A bayesian generative model for surface template estimation. Int J Biomed Imaging 2010: 10.1155/2010/974957. Epub 2010 Sep. 20.
81. Trouve A (1995) An infinite dimensional group approach for physics based models. Technical Report. In Press.
82. Miller M I, Younes L (2001) Group actions, homeomorphisms, and matching: A general framework. Int. J. Comput. Vision 41: 61-84.
83. Hammers A, Heckemann R, Koepp M J, Duncan J S, Hajnal J V, et al. (2007) Automatic detection and quantification of hippocampal atrophy on MRI in temporal lobe epilepsy: A proof-of-principle study. Neuroimage 36: 38-47.
84. Morey R A, Petty C M, Xu Y, Pannu Hayes J, Wagner II H R, et al. (2009) A comparison of automated segmentation and manual tracing for quantifying hippocampal and amygdala volumes. Neuroimage 45: 855-866.
85. Coupe P, Manjon J V, Fonov V, Pruessner J, Robles M, et al. (2011) Patch-based segmentation using expert priors: Application to hippocampus and ventricle segmentation. Neuroimage 54: 940-954.
86. Leung K K, Barnes J, Ridgway G R, Bartlett J W, Clarkson M J, et al. (2010) Automated cross-sectional and longitudinal hippocampal volume measurement in mild cognitive impairment and alzheimer's disease. Neuroimage 51: 1345-1359.
87. Lotjonen J, Wolz R, Koikkalainen J, Julkunen V, Thurfjell L, et al. (2011) Fast and robust extraction of hippocampus from MR images for diagnostics of alzheimer's disease. Neuroimage 56: 185-196.
88. Tang X, Mori S, Miller M I (2012) Segmentation via multi-atlas LDDMM. In: LANDMAN, B. A. & WARFIELD, S. K., eds. MICCAI 2012 Workshop on Multi-Atlas Labeling: 123-133.
89. Van Campenhout J, Cover T (1981) Maximum entropy and conditional probability. Information Theory, IEEE Transactions on 27: 483-489.

We claim:
1. A computer-implemented method for classifying a region of interest of a subject, comprising:
   receiving imaging data comprising at least one image element, the imaging data comprising the region of interest of the subject;
   providing a plurality of atlases, each of the plurality of atlases having a candidate region that corresponds to the region of interest of the imaging data, each of the plurality of atlases having at least one image element with associated location and property information;
   co-registering the plurality of atlases to the imaging data, using at least one processor;
   assigning a probability to generate a labeling parameter for the region of interest, the probability being associated with each atlas; and
   classifying the region of interest of the subject based on said assigning,
   wherein the probability for the labeling parameter is based on a plurality of probability terms of each atlas, the plurality of probability terms including a location value and a property value of the at least one image element of each atlas,
   wherein the location value is selected from a most probable location assignment among the plurality of atlases and wherein the property value is selected from a most probable intensity assignment from the plurality of atlases.

2. A system for classifying a region of interest of a subject, the system comprising:
- a memory storing computer-executable instructions; and
- a processor that is coupled to the memory and that is configured to execute the computer-executable instructions to perform:
- receiving imaging data comprising at least one image element, the imaging data comprising the region of interest of the subject;
- providing a plurality of atlases, each of the plurality of atlases having a candidate region that corresponds to the region of interest of the imaging data, each of the plurality of atlases having at least one image element with associated location and property information;
- co-registering the plurality of atlases to the imaging data;
- assigning a probability to generate a labeling parameter for the region of interest, the probability being associated with each atlas; and
- classifying the region of interest of the subject based on said assigning,
- wherein the probability for the labeling parameter is based on a plurality of probability terms of each atlas, the plurality of probability terms including a location value and a property value of the at least one image element of each atlas,
- wherein the location value is selected from a most probable location assignment among the plurality of atlases and wherein the property value is selected from a most probable intensity assignment from the plurality of atlases.

3. The system of claim 2, wherein the classifying includes using a predetermined formula to combine the plurality of probability terms.

4. The system of claim 3, wherein:
- the co-registering the plurality of atlases generates a mixture of probabilities from each atlas of at least one labeling parameter,
- the generated mixture of probabilities is maximized with respect to the parameter being estimated, and
- the mixture is generated via superposition and weighting of the probability from each atlas, and
- the generated mixture is used in generating the labeling parameter.

5. The system of claim 4, wherein the plurality of probability terms is generated from statistical noise modeling of an observed imager modality of the imaging data, the statistical noise modeling determining the location values and the property values.

6. The system of claim 2, wherein the labeling parameter is at least one of: size of tissue, amount of cerebrospinal fluid or type of tissue.

7. The system of claim 2, wherein the probability used in the classifying meets a predetermined statistical significance.

8. The system of claim 2, wherein for each of the plurality of atlases, the classifying incorporates:
- a weight corresponding to a function of a modality of the imaging data and the atlas.

9. The system of claim 8, wherein the weight increases as a difference in intensity between the region of interest and the corresponding candidate region of the atlas decreases.

10. The system of claim 8, wherein the weight determined using an expectation-maximization algorithm.

11. The system of claim 8, wherein the function of the modality is determined by an MRI target image modality, a measure of intensity, a vector of intensities, a matrix of intensities, or a finite alphabet valued label or a vector or a matrix of intensities or a finite alphabet valued label, or any combination thereof.

12. The system of claim 8, wherein the imaging data includes a plurality of images and the receiving includes receiving the plurality of images, and
- wherein the co-registering includes co-registering the plurality of images to the plurality of atlases.

13. The system of claim 12, wherein the weight corresponds to a function of at least two modalities of the imaging data and the plurality of atlases.

14. The system of claim 11, wherein the measure of intensity is at least one of:
- a mean intensity of the region of interest;
- a sum of intensities of the region of interest;
- a highest intensity of the region of interest;
- a lowest intensity of the region of interest;
- a vector or a matrix of any of these values; and
- a finite alphabet semantic labeling from an ontology.

15. The system of claim 2, wherein for each of the plurality of atlases, the classifying incorporates:
- a weight corresponding to a function of deformation of the image element from being mapped to the atlas.

16. The system of claim 15, wherein the weight increases as an amount of deformation of the region of interest from being mapped to the atlas decreases.

17. The system of claim 15, wherein the weight is also a function of other features that are predetermined between the imaging data and the atlas.

18. The system of claim 17, wherein the other features include non-image information of the subject and atlases, the non-image information including a function of an age of the subject of the imaging data and an age corresponding to the plurality of atlases or a diagnosis of the subject of the imaging data and a diagnosis corresponding to the plurality of atlases, or any combination thereof.

19. The system of claim 2, wherein for each of the plurality of atlases, the classifying incorporates:
- global anatomical features in the image.

20. The system of claim 2, wherein at least one of the plurality of atlases are co-registered to the imaging data using a linear transformation, a nonlinear transformation, and/or a diffeomorphic transformation.

21. The system of claim 2, wherein the at least one image element is at least one of a pixel, a plurality of pixels, a voxel, or a plurality of voxels.

22. The system of claim 2, further comprising:
- suggesting that the subject has an anatomical feature based on the classifying.

23. The system of claim 22, wherein the anatomical feature is at least one of an abnormality, a disease, a condition, a diagnosis, or any combination thereof.

24. The system of claim 2, wherein the imaging data is generated from at least one of magnetic resonance imaging (MRI), computed tomography (CT), positron emission tomography (PET), ultrasound, or nuclear tracer three-dimensional imaging.

25. The system of claim 2, wherein the region of interest comprises a portion of at least one of a brain, a heart, a liver, skin, a lung, another organ, one or more bones, or any combination thereof.

26. The system of claim 2, wherein a difference in intensities between the candidate regions of interest of the plurality of atlases and the region of interest of the imaging data is determined by determining a distance vector.

27. A non-transitory computer readable storage medium for classifying a region of interest of a subject, the computer readable storage medium comprising instructions that when executed enable a computing system to perform:

receiving imaging data comprising at least one image element, the imaging data comprising the region of interest of the subject;

providing a plurality of atlases, each of the plurality of atlases having a candidate region that corresponds to the region of interest of the imaging data, each of the plurality of atlases having at least one image element with associated location and property information;

co-registering the plurality of atlases to the imaging data, using at least one processor;

assigning a probability to generate a labeling parameter for the region of interest, the probability being associated with each atlas; and classifying the region of interest of the subject based on said assigning, wherein the probability for the labeling parameter is based on a plurality of probability terms of each atlas, the plurality of probability terms including a location value and a property value of the at least one image element of each atlas, wherein the location value is selected from a most probable location assignment among the plurality of atlases and wherein the property value is selected from a most probable intensity assignment from the plurality of atlases.

\* \* \* \* \*

UNITED STATES PATENT AND TRADEMARK OFFICE
CERTIFICATE OF CORRECTION

PATENT NO. : 10,535,133 B2
APPLICATION NO. : 15/112164
DATED : January 14, 2020
INVENTOR(S) : Michael I. Miller et al.

Page 1 of 1

It is certified that error appears in the above-identified patent and that said Letters Patent is hereby corrected as shown below:

In the Specification

Column 1, Lines 16-21:
"This invention was made with Government Support under grant Nos. RO1AG020012, R03EB04357, R01 DC011317; R01 EB000975, P41 EB015909, R01 EB008171, R01 HD065955, R21AG033774, and U01AG033655 awarded by the National Institutes of Health. The Government has certain rights in the invention." should read --This invention was made with government support under EB015909 awarded by the National Institutes of Health. The government has certain rights in the invention.--

Signed and Sealed this
Fifteenth Day of September, 2020

Andrei Iancu
*Director of the United States Patent and Trademark Office*